United States Patent
Zucherman et al.

(10) Patent No.: US 7,575,600 B2
(45) Date of Patent: Aug. 18, 2009

(54) ARTIFICIAL VERTEBRAL DISK REPLACEMENT IMPLANT WITH TRANSLATING ARTICULATION CONTACT SURFACE AND METHOD

(75) Inventors: James F. Zucherman, San Francisco, CA (US); Ken Y. Hsu, San Francisco, CA (US)

(73) Assignee: Kyphon SARL (CH)

( * ) Notice: Subject to any disclaimer, the term of this patent is extended or adjusted under 35 U.S.C. 154(b) by 775 days.

(21) Appl. No.: 11/003,624

(22) Filed: Dec. 3, 2004

(65) Prior Publication Data

US 2006/0069439 A1 Mar. 30, 2006

Related U.S. Application Data

(60) Provisional application No. 60/614,302, filed on Sep. 29, 2004.

(51) Int. Cl.
*A61F 2/44* (2006.01)
(52) U.S. Cl. .................................... 623/17.15
(58) Field of Classification Search .............. 623/17.13, 623/17.14, 17, 16
See application file for complete search history.

(56) References Cited

U.S. PATENT DOCUMENTS

| 243,286 | A | 6/1881 | McWilliam |
| 572,486 | A | 12/1896 | Horn |
| 2,261,446 | A | 11/1941 | Ormsby |
| 2,456,806 | A | 12/1948 | Wolffe |
| 2,677,369 | A | 5/1954 | Knowles |
| 2,804,936 | A | 9/1957 | Stampe |
| 3,320,951 | A | 5/1967 | Wittebol |
| 3,426,364 | A | 2/1969 | Lumb |
| 3,510,883 | A | 5/1970 | Carthcart |
| 3,648,691 | A | 3/1972 | Lumb et al. |
| 3,740,769 | A | 6/1973 | Haboush |
| 3,867,728 | A | 2/1975 | Stubstad et al. |
| 3,875,595 | A | 4/1975 | Froning |
| 3,903,549 | A | 9/1975 | Deyerle |
| 4,309,777 | A | 1/1982 | Patil |
| 4,349,921 | A | 9/1982 | Kuntz |

(Continued)

FOREIGN PATENT DOCUMENTS

CA 2015507 1/1991

(Continued)

OTHER PUBLICATIONS

*Ceramic Interspinous Block (CISB) Assisted Anterior Interbody Fusion,* Haruo Tsuji, Norikazu Hirano, Yoshiharu Katoh, Hiroshi Ohsima, Hirokazu Ishihara, Hisao Matsui,and Yohihiko Hayashi, *Journal of Spinal Disorders* vol. 3. No. 1, pp. 77-86, c1990 Raven Press, Ltd., New York.

(Continued)

*Primary Examiner*—David Isabella
*Assistant Examiner*—Suba Ganesan

(57) ABSTRACT

The present disclosure is directed to an implant that can be placed between two vertebrae using a lateral, anterior or posterior insertion method. The implant is characterized by having a first endplate and a second endplate, both endplates having inner surfaces that oppose each other when anchored into opposing vertebral bodies. The inner surfaces give rise to two articulating elements, each articulating element including two compatible units that mate and allow motion of the spine, including flexion, extension, lateral motion and rotational movement.

17 Claims, 20 Drawing Sheets

U.S. PATENT DOCUMENTS

| | | | |
|---|---|---|---|
| 4,369,769 A | 1/1983 | Edwards | |
| 4,401,112 A | 8/1983 | Rezaian | |
| 4,470,158 A | 9/1984 | Pappas et al. | |
| 4,479,491 A | 10/1984 | Martin | |
| 4,499,613 A | 2/1985 | Yarrow | |
| 4,501,269 A | 2/1985 | Bagby | |
| 4,550,450 A | 11/1985 | Kinnett | |
| 4,553,273 A | 11/1985 | Wu | |
| 4,554,914 A | 11/1985 | Kapp et al. | |
| 4,599,084 A | 7/1986 | Nashef | |
| 4,599,086 A | 7/1986 | Doty | |
| 4,622,959 A | 11/1986 | Marcus | |
| 4,636,217 A | 1/1987 | Ogilvie | |
| 4,653,487 A | 3/1987 | Maale | |
| 4,657,550 A | 4/1987 | Daher | |
| 4,681,589 A | 7/1987 | Tronzo | |
| 4,685,447 A | 8/1987 | Iversen et al. | |
| 4,696,290 A | 9/1987 | Steffee | |
| 4,714,469 A | 12/1987 | Kenna | |
| 4,743,256 A | 5/1988 | Brantigan | |
| 4,743,262 A | 5/1988 | Tronzo | |
| 4,759,766 A | 7/1988 | Büttner-Janz et al. | |
| 4,759,769 A | 7/1988 | Hedman et al. | |
| 4,772,287 A | 9/1988 | Ray et al. | |
| 4,790,303 A | 12/1988 | Steffee | |
| 4,805,607 A | 2/1989 | Engelhardt et al. | |
| 4,834,757 A | 5/1989 | Brantigan | |
| 4,863,477 A | 9/1989 | Monson | |
| 4,874,389 A | 10/1989 | Downey | |
| 4,875,474 A | 10/1989 | Border | |
| 4,878,915 A | 11/1989 | Brantigan | |
| 4,892,545 A | 1/1990 | Day et al. | |
| 4,904,260 A | 2/1990 | Ray et al. | |
| 4,904,261 A | 2/1990 | Dove et al. | |
| 4,911,718 A | 3/1990 | Lee et al. | |
| 4,932,969 A | 6/1990 | Frey et al. | |
| 4,932,975 A | 6/1990 | Main et al. | |
| 4,936,848 A | 6/1990 | Bagby | |
| 4,946,378 A | 8/1990 | Hirayama et al. | |
| 4,961,740 A | 10/1990 | Ray et al. | |
| 4,969,888 A | 11/1990 | Scholten et al. | |
| 4,997,432 A | 3/1991 | Keller | |
| 5,002,576 A | 3/1991 | Fuhrmann et al. | |
| 5,004,476 A | 4/1991 | Cook | |
| 5,011,484 A | 4/1991 | Breard | |
| 5,015,247 A | 5/1991 | Michelson | |
| 5,026,373 A | 6/1991 | Ray et al. | |
| 5,035,716 A | 7/1991 | Downey | |
| 5,037,438 A | 8/1991 | Davidson | |
| 5,047,055 A | 9/1991 | Bao et al. | |
| 5,055,104 A | 10/1991 | Ray | |
| 5,059,193 A | 10/1991 | Kuslich | |
| 5,059,194 A | 10/1991 | Michelson | |
| 5,062,850 A | 11/1991 | MacMillian et al. | |
| 5,102,954 A | 11/1991 | Albrektsson et al. | |
| 5,071,437 A | 12/1991 | Steffee | |
| 5,108,395 A | 4/1992 | Laurain | |
| 5,108,438 A | 4/1992 | Stone | |
| 5,108,442 A | 4/1992 | Smith | |
| 5,122,130 A | 6/1992 | Keller | |
| 5,123,926 A | 6/1992 | Pisharodi | |
| 5,167,662 A | 12/1992 | Hayes et al. | |
| 5,171,280 A | 12/1992 | Baumgartner | |
| 5,171,281 A | 12/1992 | Parsons et al. | |
| 5,180,381 A | 1/1993 | Aust et al. | |
| 5,192,326 A | 3/1993 | Bao et al. | |
| 5,192,327 A | 3/1993 | Brantigan | |
| 5,246,458 A | 9/1993 | Graham | |
| 5,258,031 A | 11/1993 | Salib et al. | |
| 5,258,043 A | 11/1993 | Stone | |
| 5,263,953 A | 11/1993 | Bagby | |
| 5,271,737 A | 12/1993 | Baldwin et al. | |
| 5,282,868 A | 2/1994 | Bahler | |
| 5,290,312 A | 3/1994 | Kojimoto et al. | |
| 5,306,275 A | 4/1994 | Bryan | |
| 5,306,307 A | 4/1994 | Senter | |
| 5,306,308 A | 4/1994 | Gross et al. | |
| 5,306,309 A | 4/1994 | Wagner et al. | |
| 5,313,962 A | 5/1994 | Obenchain | |
| 5,314,477 A | 5/1994 | Marnay | |
| 5,314,478 A | 5/1994 | Oka et al. | |
| 5,320,644 A | 6/1994 | Baumgartner | |
| 5,336,223 A | 8/1994 | Rogers | |
| 5,344,458 A | 9/1994 | Bonutti | |
| 5,350,397 A | 9/1994 | Palermo et al. | |
| 5,352,225 A | 10/1994 | Yuan | |
| 5,354,302 A | 10/1994 | Ko | |
| 5,360,430 A | 11/1994 | Lin | |
| 5,366,508 A | 11/1994 | Brekke | |
| 5,370,693 A | 12/1994 | Kelman et al. | |
| 5,370,697 A | 12/1994 | Baumgartner | |
| 5,375,823 A | 12/1994 | Navas | |
| 5,382,248 A | 1/1995 | Jacobson et al. | |
| 5,383,884 A | 1/1995 | Summers | |
| 5,390,683 A | 2/1995 | Pisharodi | |
| 5,395,317 A | 3/1995 | Kambin | |
| 5,395,372 A | 3/1995 | Holt et al. | |
| 5,397,364 A | 3/1995 | Kozak et al. | |
| 5,401,269 A | 3/1995 | Büttner-Janz et al. | |
| 5,415,704 A | 5/1995 | Davidson | |
| 5,423,816 A | 6/1995 | Lin | |
| 5,423,817 A | 6/1995 | Lin | |
| 5,425,772 A | 6/1995 | Brantigan | |
| 5,425,773 A | 6/1995 | Boyd et al. | |
| 5,425,777 A | 6/1995 | Sarkisian et al. | |
| 5,431,658 A | 7/1995 | Moskovich | |
| 5,439,464 A | 8/1995 | Shapiro | |
| 5,443,514 A | 8/1995 | Steffee | |
| 5,443,515 A | 8/1995 | Cohen et al. | |
| 5,445,639 A | 8/1995 | Kuslich et al. | |
| 5,454,812 A | 10/1995 | Lin | |
| 5,456,722 A | 10/1995 | McLeod et al. | |
| 5,458,638 A | 10/1995 | Kuslich et al. | |
| 5,458,641 A | 10/1995 | Ramirez Jimenez | |
| 5,458,642 A | 10/1995 | Beer et al. | |
| 5,458,643 A | 10/1995 | Oka et al. | |
| 5,480,401 A | 1/1996 | Navas | |
| 5,480,442 A | 1/1996 | Bertagnoli | |
| 5,484,437 A | 1/1996 | Michelson | |
| 5,489,307 A | 2/1996 | Kuslich et al. | |
| 5,489,308 A | 2/1996 | Kuslich et al. | |
| 5,496,318 A | 3/1996 | Howland et al. | |
| 5,505,732 A | 4/1996 | Michelson | |
| 5,507,816 A | 4/1996 | Bullivant | |
| 5,509,934 A | 4/1996 | Cohnen | |
| 5,514,180 A | 5/1996 | Heggeness et al. | |
| 5,522,899 A | 6/1996 | Michelson | |
| 5,527,312 A | 6/1996 | Ray | |
| 5,531,793 A | 7/1996 | Kelman et al. | |
| 5,534,023 A | 7/1996 | Henley | |
| 5,534,028 A | 7/1996 | Bao et al. | |
| 5,534,029 A | 7/1996 | Shima | |
| 5,534,030 A | 7/1996 | Navarro et al. | |
| 5,534,031 A | 7/1996 | Matsuzaki et al. | |
| 5,540,689 A | 7/1996 | Sanders et al. | |
| 5,545,164 A | 8/1996 | Howland | |
| 5,545,229 A | 8/1996 | Parsons et al. | |
| 5,549,679 A | 8/1996 | Kuslich | |
| 5,554,191 A | 9/1996 | Lahille et al. | |
| 5,556,431 A | 9/1996 | Büttner-Janz | |
| 5,562,736 A | 10/1996 | Ray et al. | |
| 5,562,738 A | 10/1996 | Boyd et al. | |
| 5,571,109 A | 11/1996 | Bertagnoli | |
| 5,571,189 A | 11/1996 | Kuslich | |

| | | | | | | |
|---|---|---|---|---|---|---|
| 5,571,190 | A | 11/1996 | Ulrich et al. | 5,876,404 A | 3/1999 | Zucherman et al. |
| 5,571,192 | A | 11/1996 | Schönhöffer | 5,885,292 A | 3/1999 | Moskovitz et al. |
| 5,591,165 | A | 1/1997 | Jackson | 5,885,299 A | 3/1999 | Winslow et al. |
| 5,591,235 | A | 1/1997 | Kuslich | 5,888,222 A | 3/1999 | Coates et al. |
| 5,593,409 | A | 1/1997 | Michelson | 5,888,224 A | 3/1999 | Beckers et al. |
| 5,599,279 | A | 2/1997 | Slotman et al. | 5,888,226 A | 3/1999 | Rogozinski |
| 5,601,556 | A | 2/1997 | Pisharodi | 5,888,227 A | 3/1999 | Cottle |
| 5,603,713 | A | 2/1997 | Aust et al. | 5,891,147 A | 4/1999 | Moskovitz et al. |
| 5,609,634 | A | 3/1997 | Voydeville | 5,893,889 A | 4/1999 | Harrington |
| 5,609,635 | A | 3/1997 | Michelson | 5,893,890 A | 4/1999 | Pisharodi |
| 5,609,636 | A | 3/1997 | Kohrs et al. | 5,895,426 A | 4/1999 | Scarborough et al. |
| 5,609,638 | A | 3/1997 | Price et al. | 5,895,427 A | 4/1999 | Kuslich et al. |
| 5,620,458 | A | 4/1997 | Green et al. | 5,895,428 A | 4/1999 | Berry |
| 5,645,592 | A | 7/1997 | Nicolais et al. | 5,899,941 A | 5/1999 | Nishijima et al. |
| 5,645,596 | A | 7/1997 | Kim et al. | 5,906,616 A | 5/1999 | Pavlov et al. |
| 5,645,597 | A | 7/1997 | Krapiva | 5,919,235 A | 7/1999 | Husson et al. |
| 5,645,598 | A | 7/1997 | Brosnahan, III | 5,928,284 A | 7/1999 | Mehdizadeh |
| 5,645,599 | A | 7/1997 | Samani | 5,944,754 A | 8/1999 | Vacanti |
| 5,653,761 | A | 8/1997 | Pisharodi | 5,945,115 A | 8/1999 | Dunn et al. |
| 5,653,762 | A | 8/1997 | Pisharodi | 5,961,554 A | 10/1999 | Jamson et al. |
| 5,658,285 | A | 8/1997 | Marnay et al. | 5,964,807 A | 10/1999 | Gan et al. |
| 5,658,335 | A | 8/1997 | Allen | 5,976,186 A | 11/1999 | Bao et al. |
| 5,658,336 | A | 8/1997 | Pisharodi | 5,980,572 A | 11/1999 | Kim et al. |
| 5,658,337 | A | 8/1997 | Kohrs et al. | 5,984,967 A | 11/1999 | Zdeblick et al. |
| 5,658,347 | A | 8/1997 | Sarkisian et al. | 5,989,291 A | 11/1999 | Ralph et al. |
| 5,665,122 | A | 9/1997 | Kambin | 6,001,130 A | 12/1999 | Bryan et al. |
| 5,669,909 | A | 9/1997 | Zdeblick et al. | 6,004,573 A | 12/1999 | Rathi et al. |
| 5,674,294 | A | 10/1997 | Bainville et al. | 6,005,162 A | 12/1999 | Constantz |
| 5,674,295 | A | 10/1997 | Ray et al. | 6,010,502 A | 1/2000 | Bagby |
| 5,674,296 | A | 10/1997 | Bryan et al. | 6,019,792 A | 2/2000 | Cauthen |
| 5,676,701 | A | 10/1997 | Yuan et al. | 6,019,793 A | 2/2000 | Perren et al. |
| 5,676,702 | A | 10/1997 | Ratron | 6,022,376 A | 2/2000 | Assell et al. |
| 5,683,394 | A | 11/1997 | Rinner | 6,030,389 A | 2/2000 | Wagner et al. |
| 5,683,463 | A | 11/1997 | Godefroy et al. | 6,039,761 A | 3/2000 | Li et al. |
| 5,683,464 | A | 11/1997 | Wagner et al. | 6,039,763 A | 3/2000 | Shelokov |
| 5,683,465 | A | 11/1997 | Shinn et al. | 6,042,582 A | 3/2000 | Ray |
| 5,693,100 | A | 12/1997 | Pisharodi | 6,045,579 A | 4/2000 | Hochshuler et al. |
| 5,697,889 | A | 12/1997 | Slotman et al. | 6,045,580 A | 4/2000 | Scarborough et al. |
| 5,697,977 | A | 12/1997 | Pisharodi | 6,048,342 A | 4/2000 | Zucherman et al. |
| 5,700,292 | A | 12/1997 | Margulies | 6,051,648 A | 4/2000 | Rhee et al. |
| 5,702,449 | A | 12/1997 | McKay | 6,063,121 A | 5/2000 | Xavier |
| 5,702,450 | A | 12/1997 | Bisserie | 6,068,630 A | 5/2000 | Zucherman et al. |
| 5,702,454 | A | 12/1997 | Baumgartner | 6,074,390 A | 6/2000 | Zucherman et al. |
| 5,702,455 | A | 12/1997 | Saggar | 6,080,155 A | 6/2000 | Michelson |
| 5,702,469 | A | 12/1997 | Whipple et al. | 6,080,158 A | 6/2000 | Lin |
| 5,709,683 | A | 1/1998 | Bagby | 6,080,193 A | 6/2000 | Hochshuler et al. |
| 5,716,415 | A | 2/1998 | Steffee | 6,086,613 A | 7/2000 | Camino et al. |
| 5,716,416 | A | 2/1998 | Lin | 6,090,112 A | 7/2000 | Zucherman et al. |
| 5,741,253 | A | 4/1998 | Michelson | 6,093,205 A | 7/2000 | McLeod et al. |
| 5,755,732 | A | 5/1998 | Green et al. | 6,096,038 A | 8/2000 | Michelson |
| 5,755,796 | A | 5/1998 | Ibo et al. | 6,096,080 A | 8/2000 | Nicholson et al. |
| 5,755,798 | A | 5/1998 | Papavero et al. | 6,099,531 A | 8/2000 | Bonutti |
| 5,755,811 | A | 5/1998 | Tanamal et al. | 6,102,950 A | 8/2000 | Vaccaro |
| 5,766,252 | A | 6/1998 | Henry et al. | 6,110,210 A | 8/2000 | Norton et al. |
| 5,772,661 | A | 6/1998 | Michelson | 6,111,164 A | 8/2000 | Rainey et al. |
| 5,776,196 | A | 7/1998 | Matsuzaki et al. | 6,113,637 A | 9/2000 | Gill et al. |
| 5,776,199 | A | 7/1998 | Michelson | 6,113,638 A | 9/2000 | Williams et al. |
| 5,782,830 | A | 7/1998 | Farris | 6,113,639 A | 9/2000 | Ray et al. |
| 5,782,832 | A | 7/1998 | Larsen et al. | 6,120,502 A | 9/2000 | Michelson |
| 5,782,919 | A | 7/1998 | Zdeblick et al. | 6,120,503 A | 9/2000 | Michelson |
| 5,797,909 | A | 8/1998 | Michelson | 6,123,705 A | 9/2000 | Michelson |
| 5,800,438 | A | 9/1998 | Tuke et al. | 6,126,689 A | 10/2000 | Brett |
| 5,800,547 | A | 9/1998 | Schafer et al. | 6,127,597 A | 10/2000 | Beyar et al. |
| 5,800,550 | A | 9/1998 | Sertich | 6,129,763 A | 10/2000 | Chauvin et al. |
| 5,824,093 | A | 10/1998 | Ray et al. | 6,132,430 A | 10/2000 | Wagner |
| 5,824,094 | A | 10/1998 | Serhan et al. | 6,132,465 A | 10/2000 | Ray et al. |
| 5,827,328 | A | 10/1998 | Buttermann | 6,136,001 A | 10/2000 | Michelson |
| 5,836,948 | A | 11/1998 | Zucherman et al. | 6,136,031 A | 10/2000 | Middleton |
| 5,860,973 | A | 1/1999 | Michelson | 6,139,579 A | 10/2000 | Steffee et al. |
| 5,860,977 | A | 1/1999 | Zucherman et al. | 6,146,421 A | 11/2000 | Gordon et al. |
| 5,865,845 | A | 2/1999 | Thalgott | 6,146,422 A | 11/2000 | Lawson |
| 5,865,846 | A | 2/1999 | Bryan et al. | 6,149,650 A | 11/2000 | Michelson |
| 5,865,848 | A | 2/1999 | Baker | 6,149,652 A | 11/2000 | Zucherman et al. |

| | | | | | | |
|---|---|---|---|---|---|---|
| 6,149,686 | A | 11/2000 | Kuslich et al. | 6,402,785 B1 | 6/2002 | Zdeblick et al. |
| 6,152,926 | A | 11/2000 | Zucherman et al. | 6,409,766 B1 | 6/2002 | Brett |
| 6,156,038 | A | 12/2000 | Zucherman et al. | 6,413,278 B1 | 7/2002 | Marchosky |
| 6,156,067 | A | 12/2000 | Bryan et al. | 6,416,551 B1 | 7/2002 | Keller |
| 6,159,215 | A | 12/2000 | Urbahns et al. | 6,419,676 B1 | 7/2002 | Zucherman et al. |
| 6,162,252 | A | 12/2000 | Kuras et al. | 6,419,677 B2 | 7/2002 | Zucherman et al. |
| 6,165,218 | A | 12/2000 | Husson et al. | 6,419,704 B1 | 7/2002 | Ferree |
| 6,176,882 | B1 | 1/2001 | Biedermann et al. | 6,419,706 B1 | 7/2002 | Graf |
| 6,179,874 | B1 | 1/2001 | Cauthen | 6,423,063 B1 | 7/2002 | Bonutti |
| 6,183,471 | B1 | 2/2001 | Zucherman et al. | 6,423,095 B1 | 7/2002 | Van Hoech et al. |
| 6,190,387 | B1 | 2/2001 | Zucherman et al. | 6,425,920 B1 | 7/2002 | Hamada |
| 6,190,414 | B1 | 2/2001 | Young et al. | 6,432,106 B1 | 8/2002 | Fraser |
| 6,193,757 | B1 | 2/2001 | Foley et al. | 6,436,098 B1 | 8/2002 | Michelson |
| 6,206,879 | B1 | 3/2001 | Marnay et al. | 6,436,119 B1 | 8/2002 | Erb et al. |
| 6,206,922 | B1 | 3/2001 | Zdeblick et al. | 6,436,140 B1 | 8/2002 | Liu et al. |
| 6,210,412 | B1 | 4/2001 | Michelson | 6,436,142 B1 | 8/2002 | Paes et al. |
| 6,224,595 | B1 | 5/2001 | Michelson | 6,440,139 B2 | 8/2002 | Michelson |
| 6,224,607 | B1 | 5/2001 | Michelson | 6,440,168 B1 | 8/2002 | Cauthen |
| 6,224,631 | B1 | 5/2001 | Kohrs | 6,440,169 B1 | 8/2002 | Elberg et al. |
| 6,228,118 | B1 | 5/2001 | Gordon | 6,443,990 B1 | 9/2002 | Aebi et al. |
| 6,231,609 | B1 | 5/2001 | Mehdizadeh | 6,447,512 B1 | 9/2002 | Landry et al. |
| 6,234,705 | B1 | 5/2001 | Troxell | 6,447,544 B1 | 9/2002 | Michelson |
| 6,235,030 | B1 | 5/2001 | Zucherman et al. | 6,447,547 B1 | 9/2002 | Michelson |
| 6,238,397 | B1 | 5/2001 | Zucherman et al. | 6,451,019 B1 | 9/2002 | Zucherman et al. |
| 6,241,769 | B1 | 6/2001 | Nicholson et al. | 6,451,020 B1 | 9/2002 | Zucherman et al. |
| 6,241,770 | B1 | 6/2001 | Michelson | 6,454,804 B1 | 9/2002 | Ferree |
| 6,241,771 | B1 | 6/2001 | Gresser et al. | 6,454,807 B1 | 9/2002 | Jackson |
| 6,245,072 | B1 | 6/2001 | Zdeblick et al. | 6,456,805 B2 | 9/2002 | Buttles et al. |
| 6,245,108 | B1 | 6/2001 | Biscup | 6,458,131 B1 | 10/2002 | Ray |
| 6,251,140 | B1 | 6/2001 | Marino et al. | 6,458,159 B1 | 10/2002 | Thalgott |
| 6,258,125 | B1 | 7/2001 | Paul et al. | 6,461,359 B1 | 10/2002 | Tribus et al. |
| 6,261,296 | B1 | 7/2001 | Aebi et al. | 6,468,310 B1 | 10/2002 | Ralph et al. |
| 6,264,655 | B1 | 7/2001 | Pisharodi | 6,471,724 B2 | 10/2002 | Zdeblick et al. |
| 6,264,656 | B1 | 7/2001 | Michelson | 6,475,219 B1 | 11/2002 | Shelokov |
| 6,264,695 | B1 | 7/2001 | Stoy | 6,478,796 B2 | 11/2002 | Zucherman et al. |
| 6,270,498 | B1 | 8/2001 | Michelson | 6,478,822 B1 | 11/2002 | Leroux et al. |
| 6,277,149 | B1 | 8/2001 | Boyle et al. | 6,478,823 B1 | 11/2002 | Michelson |
| 6,280,444 | B1 | 8/2001 | Zucherman et al. | 6,482,233 B1 | 11/2002 | Aebi et al. |
| 6,280,475 | B1 | 8/2001 | Bao et al. | 6,482,235 B1 | 11/2002 | Lambrecht et al. |
| 6,287,343 | B1 | 9/2001 | Kuslich et al. | 6,485,517 B1 | 11/2002 | Michelson |
| 6,290,724 | B1 | 9/2001 | Marino | 6,488,710 B2 | 12/2002 | Besselink |
| 6,296,664 | B1 | 10/2001 | Middleton | 6,500,178 B2 | 12/2002 | Zucherman et al. |
| 6,296,665 | B1 | 10/2001 | Strnad et al. | 6,500,205 B1 | 12/2002 | Michelson |
| 6,302,914 | B1 | 10/2001 | Michelson | 6,503,279 B1 | 1/2003 | Webb et al. |
| 6,309,421 | B1 | 10/2001 | Pisharodi | 6,514,256 B2 | 2/2003 | Zucherman et al. |
| 6,311,562 | B1 | 11/2001 | Hanada | 6,517,544 B1 | 2/2003 | Michelson |
| 6,315,795 | B1 | 11/2001 | Scarborough et al. | 6,517,580 B1 | 2/2003 | Ramadan et al. |
| 6,315,797 | B1 | 11/2001 | Middleton | 6,520,993 B2 | 2/2003 | James et al. |
| 6,325,827 | B1 | 12/2001 | Lin | 6,520,996 B1 | 2/2003 | Manasas et al. |
| 6,332,882 | B1 | 12/2001 | Zucherman et al. | 6,524,312 B2 | 2/2003 | Landry et al. |
| 6,332,883 | B1 | 12/2001 | Zucherman et al. | 6,527,773 B1 | 3/2003 | Lin et al. |
| 6,332,894 | B1 | 12/2001 | Stalcup et al. | 6,527,804 B1 | 3/2003 | Gauchet et al. |
| 6,342,074 | B1 | 1/2002 | Simpson | 6,527,806 B2 | 3/2003 | Ralph et al. |
| 6,348,071 | B1 | 2/2002 | Steffee et al. | 6,530,933 B1 | 3/2003 | Yeung et al. |
| 6,350,283 | B1 | 2/2002 | Michelson | 6,530,955 B2 | 3/2003 | Boyle et al. |
| 6,364,880 | B1 | 4/2002 | Michelson | 6,540,785 B1 | 4/2003 | Gill et al. |
| 6,366,350 | B1 | 4/2002 | Thornburg et al. | 6,547,823 B2 | 4/2003 | Scarborough et al. |
| 6,368,350 | B1 | 4/2002 | Erickson et al. | 6,548,002 B2 | 4/2003 | Gresser et al. |
| 6,368,351 | B1 | 4/2002 | Glenn et al. | 6,554,863 B2 | 4/2003 | Paul et al. |
| 6,368,353 | B1 | 4/2002 | Arcand | 6,558,386 B1 | 5/2003 | Cragg |
| 6,371,984 | B1 | 4/2002 | Van Dyke et al. | 6,558,387 B2 | 5/2003 | Errico et al. |
| 6,371,988 | B1 | 4/2002 | Pafford et al. | 6,558,390 B2 | 5/2003 | Cragg |
| 6,371,989 | B1 | 4/2002 | Chauvin et al. | 6,558,423 B1 | 5/2003 | Michelson |
| 6,375,681 | B1 | 4/2002 | Truscott | 6,558,424 B2 | 5/2003 | Thalgott |
| 6,379,355 | B1 | 4/2002 | Zucherman et al. | 6,562,045 B2 | 5/2003 | Gil et al. |
| 6,379,385 | B1 | 4/2002 | Kalas et al. | 6,562,073 B2 | 5/2003 | Foley |
| 6,383,221 | B1 | 5/2002 | Scarborough et al. | 6,562,074 B2 | 5/2003 | Gerbec et al. |
| 6,391,030 | B1 | 5/2002 | Wagner et al. | 6,565,570 B2 | 5/2003 | Sterett et al. |
| 6,391,058 | B1 | 5/2002 | Kuslich et al. | 6,569,201 B2 | 5/2003 | Moumene et al. |
| 6,395,030 | B1 | 5/2002 | Songer et al. | 6,572,653 B1 | 6/2003 | Simonson |
| 6,395,031 | B1 | 5/2002 | Foley et al. | 6,572,654 B1 | 6/2003 | Santilli |
| 6,395,032 | B1 | 5/2002 | Gauchet | 6,575,982 B1 | 6/2003 | Bonutti |
| 6,395,034 | B1 | 5/2002 | Suddaby | 6,576,016 B1 | 6/2003 | Hochshuler et al. |

| | | |
|---|---|---|
| 6,576,017 B2 | 6/2003 | Foley et al. |
| 6,579,318 B2 | 6/2003 | Varga et al. |
| 6,579,320 B1 | 6/2003 | Gauchet et al. |
| 6,579,321 B1 | 6/2003 | Gordon et al. |
| 6,582,432 B1 | 6/2003 | Michelson |
| 6,582,437 B2 | 6/2003 | Dorchak et al. |
| 6,582,468 B1 | 6/2003 | Gauchet |
| 6,607,558 B2 | 8/2003 | Kuras |
| 6,610,089 B1 | 8/2003 | Liu et al. |
| 6,610,093 B1 * | 8/2003 | Pisharodi .................. 623/17.15 |
| 6,626,944 B1 | 9/2003 | Taylor |
| 6,641,614 B1 | 11/2003 | Wagner et al. |
| 6,682,562 B2 | 1/2004 | Viart et al. |
| 6,692,501 B2 | 2/2004 | Michelson |
| 6,699,246 B2 | 3/2004 | Zucherman et al. |
| 6,706,068 B2 | 3/2004 | Ferree |
| 6,706,070 B1 | 3/2004 | Wagner et al. |
| 6,740,118 B2 | 5/2004 | Eisermann et al. |
| 6,749,612 B1 | 6/2004 | Conchy et al. |
| 6,749,635 B1 | 6/2004 | Bryan |
| 6,755,841 B2 | 6/2004 | Fraser et al. |
| 6,770,095 B2 | 8/2004 | Grinberg et al. |
| 6,796,678 B2 | 9/2004 | Moon |
| 6,893,466 B2 | 5/2005 | Trieu |
| 6,921,403 B2 | 7/2005 | Cragg et al. |
| 6,936,071 B1 | 8/2005 | Marney et al. |
| 6,954,665 B2 | 10/2005 | Pfeiffer |
| 6,964,665 B2 | 11/2005 | Thomas et al. |
| 6,966,929 B2 | 11/2005 | Mitchell |
| 6,994,727 B2 | 2/2006 | Khandkar et al. |
| 7,048,766 B2 | 5/2006 | Ferree |
| 7,056,344 B2 | 6/2006 | Huppert et al. |
| 7,083,649 B2 | 8/2006 | Zucherman et al. |
| 7,101,375 B2 | 9/2006 | Zucherman et al. |
| 7,105,024 B2 | 9/2006 | Richelsoph |
| 7,118,580 B1 | 10/2006 | Beyersdorff et al. |
| 7,179,294 B2 | 2/2007 | Eisermann et al. |
| 7,326,250 B2 | 2/2008 | Beaurain et al. |
| 2001/0012938 A1 | 8/2001 | Zucherman et al. |
| 2002/0077702 A1 | 6/2002 | Castro |
| 2002/0107572 A1 | 8/2002 | Foley |
| 2002/0120270 A1 | 8/2002 | Trieu |
| 2002/0128715 A1 | 9/2002 | Bryan et al. |
| 2003/0069586 A1 | 4/2003 | Errico et al. |
| 2003/0074068 A1 | 4/2003 | Errico |
| 2003/0097134 A1 | 5/2003 | Kunzler |
| 2003/0176923 A1 | 9/2003 | Keller et al. |
| 2003/0191534 A1 | 10/2003 | Viart et al. |
| 2003/0204261 A1 | 10/2003 | Eisermann et al. |
| 2003/0208273 A1 | 11/2003 | Eisermann et al. |
| 2003/0233097 A1 | 12/2003 | Ferree |
| 2003/0236571 A1 | 12/2003 | Ralph |
| 2004/0002759 A1 | 1/2004 | Ferree |
| 2004/0034421 A1 | 2/2004 | Errico et al. |
| 2004/0034426 A1 | 2/2004 | Errico et al. |
| 2004/0039384 A1 | 2/2004 | Boehm et al. |
| 2004/0049279 A1 | 3/2004 | Servain |
| 2004/0073312 A1 | 4/2004 | Eisermann et al. |
| 2004/0073313 A1 | 4/2004 | Link et al. |
| 2004/0106998 A1 | 6/2004 | Ferree |
| 2004/0117022 A1 | 6/2004 | Marnay et al. |
| 2004/0138749 A1 | 7/2004 | Zucherman et al. |
| 2004/0138750 A1 | 7/2004 | Mitchell |
| 2004/0143332 A1 | 7/2004 | Krueger |
| 2004/0153157 A1 | 8/2004 | Keller |
| 2004/0225360 A1 | 11/2004 | Malone |
| 2004/0225363 A1 | 11/2004 | Richelsoph |
| 2004/0225365 A1 | 11/2004 | Eisemann et al. |
| 2004/0225366 A1 | 11/2004 | Eisermann et al. |
| 2004/0230307 A1 | 11/2004 | Eisermann et al. |
| 2004/0243240 A1 | 12/2004 | Beaurain et al. |
| 2005/0021145 A1 | 1/2005 | De Villers et al. |
| 2005/0043802 A1 | 2/2005 | Eisemann et al. |
| 2005/0065611 A1 | 3/2005 | Huppert et al. |
| 2005/0102029 A1 | 5/2005 | Blain |
| 2005/0125065 A1 | 6/2005 | Zucherman |
| 2005/0154462 A1 | 7/2005 | Zucherman et al. |
| 2005/0159818 A1 | 7/2005 | Blain |
| 2005/0159819 A1 | 7/2005 | McComack |
| 2005/0256579 A1 | 11/2005 | Keller et al. |
| 2005/0267581 A1 | 12/2005 | Marnay et al. |
| 2005/0283237 A1 | 12/2005 | Zucherman |
| 2006/0004377 A1 | 1/2006 | Keller |
| 2006/0036326 A1 | 2/2006 | Baumgartner et al. |

FOREIGN PATENT DOCUMENTS

| | | |
|---|---|---|
| CH | 624573 A5 | 8/1981 |
| DE | 2804936 A1 | 2/1979 |
| DE | 3023353 A1 | 9/1981 |
| DE | 3113142 | 1/1982 |
| DE | 4012622 | 7/1991 |
| EP | 0307241 B1 | 3/1989 |
| EP | 322334 | 6/1989 |
| EP | 0 560 140 | 2/1993 |
| EP | 0 560 141 | 2/1993 |
| EP | 0 747 025 | 12/1996 |
| EP | 0 820 740 | 1/1998 |
| EP | 1 103 237 | 5/2001 |
| EP | 1222900 | 7/2002 |
| FR | 2724108 A1 | 2/1994 |
| FR | 2705227 | 11/1994 |
| FR | 2707864 | 1/1995 |
| FR | 2717066 | 9/1995 |
| FR | 2717068 | 9/1995 |
| FR | 2718635 A1 | 10/1995 |
| FR | 2742653 A1 | 12/1995 |
| FR | 2722088 | 1/1996 |
| FR | 2722980 | 2/1996 |
| FR | 2724554 | 3/1996 |
| FR | 2730156 A1 | 8/1996 |
| FR | 2 734 148 | 11/1996 |
| FR | 2742653 | 6/1997 |
| FR | 2780269 A1 | 12/1999 |
| FR | 2806614 A1 | 9/2001 |
| GB | 780652 | 8/1957 |
| JP | 2261446 | 10/1990 |
| WO | WO 90/00037 | 1/1990 |
| WO | WO 95/31158 A | 11/1995 |
| WO | WO 99 00074 | 1/1999 |
| WO | WO 99 05995 | 2/1999 |
| WO | WO 99/26562 | 6/1999 |
| WO | WO 9953871 | 10/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/23015 A1 | 4/2000 |
| WO | WO 0042954 | 7/2000 |
| WO | WO 01/01893 A1 | 1/2001 |
| WO | WO0101893 | 1/2001 |
| WO | WO 0101893 | 1/2001 |
| WO | WO 0119295 | 3/2001 |
| WO | WO0119295 | 3/2001 |
| WO | WO 01/89428 A2 | 11/2001 |
| WO | WO0189248 | 11/2001 |
| WO | WO 0247587 | 6/2002 |
| WO | WO03039400 | 5/2003 |
| WO | WO 2004071359 | 8/2004 |
| WO | WO2004018015 | 12/2004 |

OTHER PUBLICATIONS

*Instrumentation and Implants for Spinal Surgery*,J. Dabb, *Diary of the XVIIIth Scientific Meeting of the PTO Tr/Pamietnik XVIII Zjazdu Naukowego PTO Tr/PZ, WL, Warszawa*, Link America Inc., 1971, 665.

*Spinal Stenosis and Neurogenic Claudication*, Richard W. Porter, MD, FRCS, FRCSE, *Spine* vol. 21, No. 17, pp. 2046-2052, c1996, Lippincott-Raven Publishers.

*Preliminary Design and Experimental Studies of a Novel Soft Implant for Correcting Sagittal Plan Instability in the Lumbar Spine*, R.J.Minns, BEng, Msc, PhD, DscTech, and W.K.Walsh, FRCS, *Spine* vol. 22, No. 16, pp. 1819-1827, c1997, Lippincott-Raven Publishers.

Viscoglioski Bro., LLC, Spine Arthoplasty: Market Potential & Technology Update, Spine Industry Analysis Series, Nov. 2001, pp. 1-215.

Jeanette E. Ahrens, PhD, Alexis P. Shelokov, MD, Jeffrey L. Carver, BS, Normal Joint Mobility is Maintained with an Artifical Disc Prothesis, Texas Health Research Institute, Plano, Texas, HCA Columbia Hospital, Plano, Texas, Joint Biomedical Engineering Program.

T. Hoogland, A. D. Steffe, J.D. Black, A.S. Greenwald, Cleveland Clinic Foundation, 24 Annual ORS Dallas, Texas, Feb. 21-23, 1978.

David S. Hungerford, M.D., Kenneth A. Krackow, M.D., Robert V. Kenna, Total Knee Arthoplasty: A Comprehensive Approach, Williams & Williams, Baltimore, MD., 1984, Chapter 5, pp. 71-88.

David S. Hungerford, M.D., and Robert V. Kenna, Preliminary Experience with a Total Knee Prothesis with Porous Coating Used Without Cement, J.B. Lippincott, Co., No. 176, Jun. 1983, pp. 95-107.

AB Swanson, GD Swanson, T Powers, MA Khalil, BK Maupin, DE Mayhew and SH Moss, The Journal of Bone & Joint Surgery: Unicompartmental and bicompartmental arthroplasty of the knee with a finned metal tibial-plateau implant, vol. 67-A, No. 8, October.

The Journal of Bone and Joint Surgery, Sep. 1971, American Volume, vol. 53-A, No. 6, Zimmer, Warsaw, Indiana, U.S.A., Zimmer of Canada, Ltd.

The Journal of Bone and Joint Surgery, Jul. 1970, American Volume, vol. 52-A, No. 5, Zimmer, Warsaw, Indiana, U.S.A., Zimmer of Canada, Ltd.

A.H. Crenshaw, Cambell's Operative Orthopedics, Seventh Edition, vol. Two, The C.V. Mosby Company, copyright, 1987.

TH Marnay, L'Arthoplatie Intervertebral Lombaire, Orthopedic Sugeon, Kennedy Clinic, 30000 Nimes.

TH Marnay, English translation of "L'Arthoplatie Intervertebral Lombaire.", Kennedy Clinic, 30000 Nimes.

Nobou, English translation of JP 2261446.

Grosse, English translation of FR 2742653.

Patent Cooperation Treaty—European Patent Office, "Notification of Transmittal of the International Search Report and the Written Opinion of the International Searching Authority or the Declaration,"International Application No. PC/US2005015581, Aug. 25, 2005. 7.

T.Hoggland et al, "Total Lumbar Intervertebral Disc Replacement : Testing of a New Articulating Spacer in Human Cadaver Spines," 24th Annual ORS, Feb. 21-23, 1978, p. 102, Dallas, Texas.

Medtronic Sofamor Dane, "Maverick Total Disc Replacement", brochure, published Dec. 2002, pp. 1-6.

* cited by examiner

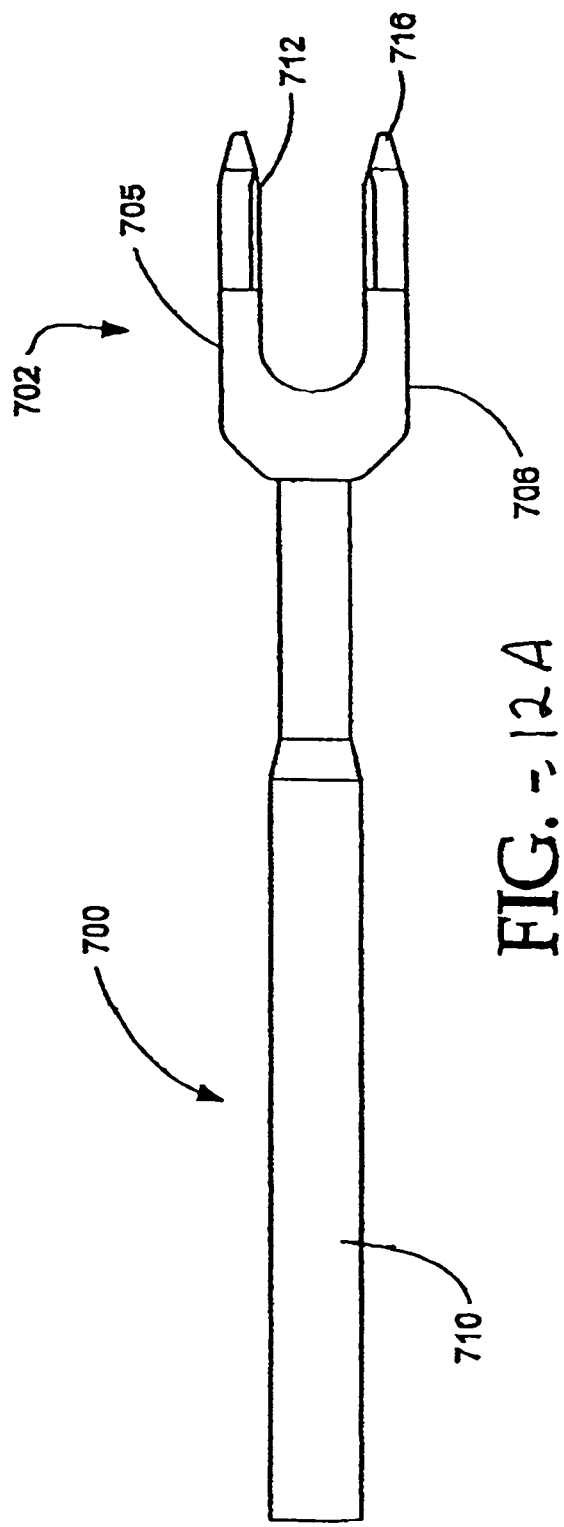
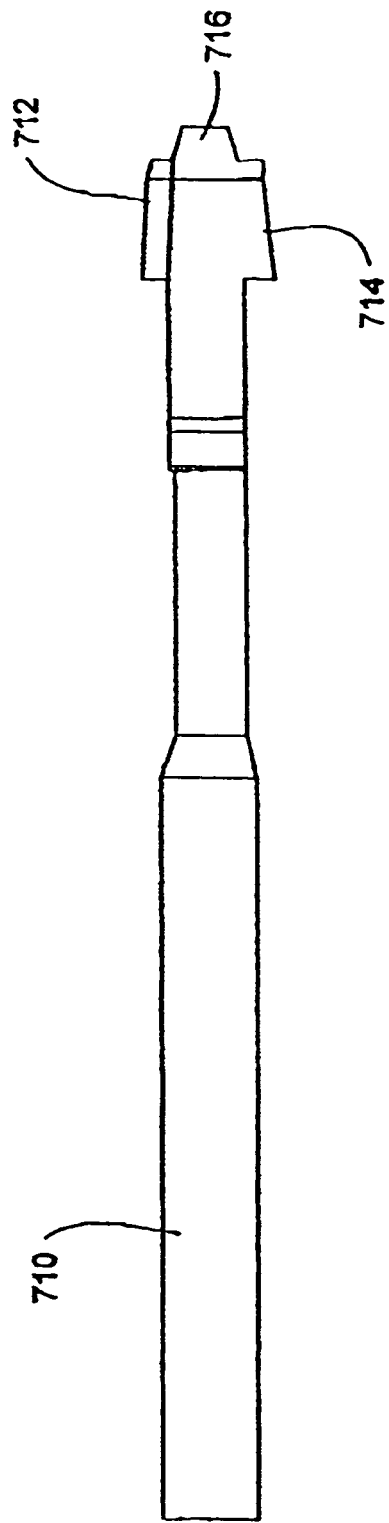
FIG. - 12A
FIG. - 12B

ARTIFICIAL VERTEBRAL DISK REPLACEMENT IMPLANT WITH TRANSLATING ARTICULATION CONTACT SURFACE AND METHOD

PRIORITY CLAIM

This application claims priority to U.S. Provisional Patent Application No. 60/614,302 entitled: ARTIFICIAL VERTEBRAL DISK REPLACEMENT IMPLANT WITH TRANSLATING ARTICULATION CONTACT SURFACE AND METHOD, by Zucherman et al., filed Sep. 29, 2004.

CROSS-REFERENCE TO RELATED APPLICATIONS

This application is related to the following co-pending applications which are each hereby incorporated by reference in their entirety:

POSTERIOR APPROACH IMPLANT METHOD FOR ASSEMBLY OF A MULTI-PIECE ARTIFICIAL SPINAL DISK REPLACEMENT DEVICE IN SITU, U.S. Provisional Patent Application No. 60/614,181, filed on Sep. 29, 2004, 2004, Inventors: James Zucherman and Ken Y. Hsu.

MULTI-PIECE ARTIFICIAL SPINAL DISK REPLACEMENT DEVICE WITH SELECTABLY POSITIONING ARTICULATING ELEMENT, U.S. Provisional Patent Application No. 60/614,246, filed on Sep. 29, 2004, Inventors: James Zucherman and Ken Y. Hsu.

MULTI-PIECE ARTIFICIAL SPINAL DISK REPLACEMENT DEVICE WITH MULTI-SEGMENTED SUPPORT PLATES, U.S. Patent Application No. 60/614,061, filed on Sep. 29, 2004, Inventors: James Zucherman and Ken Y. Hsu.

FIELD OF ART

This field of art of this disclosure is directed to an artificial vertebral disk replacement and method.

BACKGROUND

The spinal column is a biomechanical structure composed primarily of ligaments, muscles, vertebrae and intervertebral disks. The biomechanical functions of the spine include: (1) support of the body, which involves the transfer of the weight and the bending movements of the head, trunk and arms to the pelvis and legs, (2) complex physiological motion between these parts, and (3) protection of the spinal cord and nerve roots.

As the present society ages, it is anticipated that there will be an increase in adverse spinal conditions which are characteristic of aging. For example, with aging comes an increase in spinal stenosis (including, but not limited to, central canal and lateral stenosis), and facet joint degeneration. Spinal stenosis typically results from the thickening of the bones that make up the spinal column and is characterized by a reduction in the available space for the passage of blood vessels and nerves. Facet joint degeneration results from the constant load borne by the facet joints, and the eventual wear that results. Pain associated with both conditions can be relieved by medication and/or surgery.

In addition, to spinal stenosis, and facet joint degeneration, the incidence of damage to the intervertebral disks is also common. The primary purpose of the intervertebral disk is to act as a shock absorber. The disk is constructed of an inner gel-like structure, the nucleus pulposus (the nucleus), and an outer rigid structure comprised of collagen fibers, the annulus fibrosus (the annulus). At birth, the disk is 80% water, and then gradually diminishes with time, becoming stiff. With age, disks may degenerate, and bulge, thin, herniate, or ossify. Additionally, damage to disks may occur as a result disease, trauma or injury to the spine.

The damage to disks may call for a range of restorative procedures. If the damage is not extensive, repair may be indicated, while extensive damage may indicate full replacement. Regarding the evolution of restoration of damage to intervertebral disks, rigid fixation procedures resulting in fusion are still the most commonly performed surgical intervention. However, trends suggest a move away from such procedures. Currently, areas evolving to address the shortcomings of fusion for remediation of disk damage include technologies and procedures that preserve or repair the annulus, that replace or repair the nucleus, and that advance implants for total disk replacement. The trend away from fusion is driven both by issues concerning the quality of life for those suffering from damaged intervertebral disks, as well as responsible health care management. These issues drive the desire for procedures that are minimally invasive, can be tolerated by patients of all ages, especially seniors, and can be performed preferably on an out patient basis.

Most recently, there has been an increased interest in total disk replacement technology. A number of artificial disks are beginning to appear in the medical device marketplace. These artificial disks vary greatly in shape, design and functionality. With these devices go tools and methods for insertion between vertebrae thereof. Though currently the most methods of insertion of disk replacement implants include the anterior and posterior approaches, other surgical procedures, such as the lateral approach, are evolving.

Accordingly, there is a need in the art for innovation in technologies and methods that advance the art in the area of intervertebral disk replacement. This not only enhances the quality of life for those suffering from the condition, but is responsive to the current needs of health care management.

BRIEF DESCRIPTION OF THE DRAWINGS

FIG. 12A is a top view of an embodiment of a cutting tool of the invention used to prepare the vertebral bodies for the implant. FIG. 12B is a side view of the embodiment of the cutting tool of the invention.

DETAILED DESCRIPTION

Figure 1:
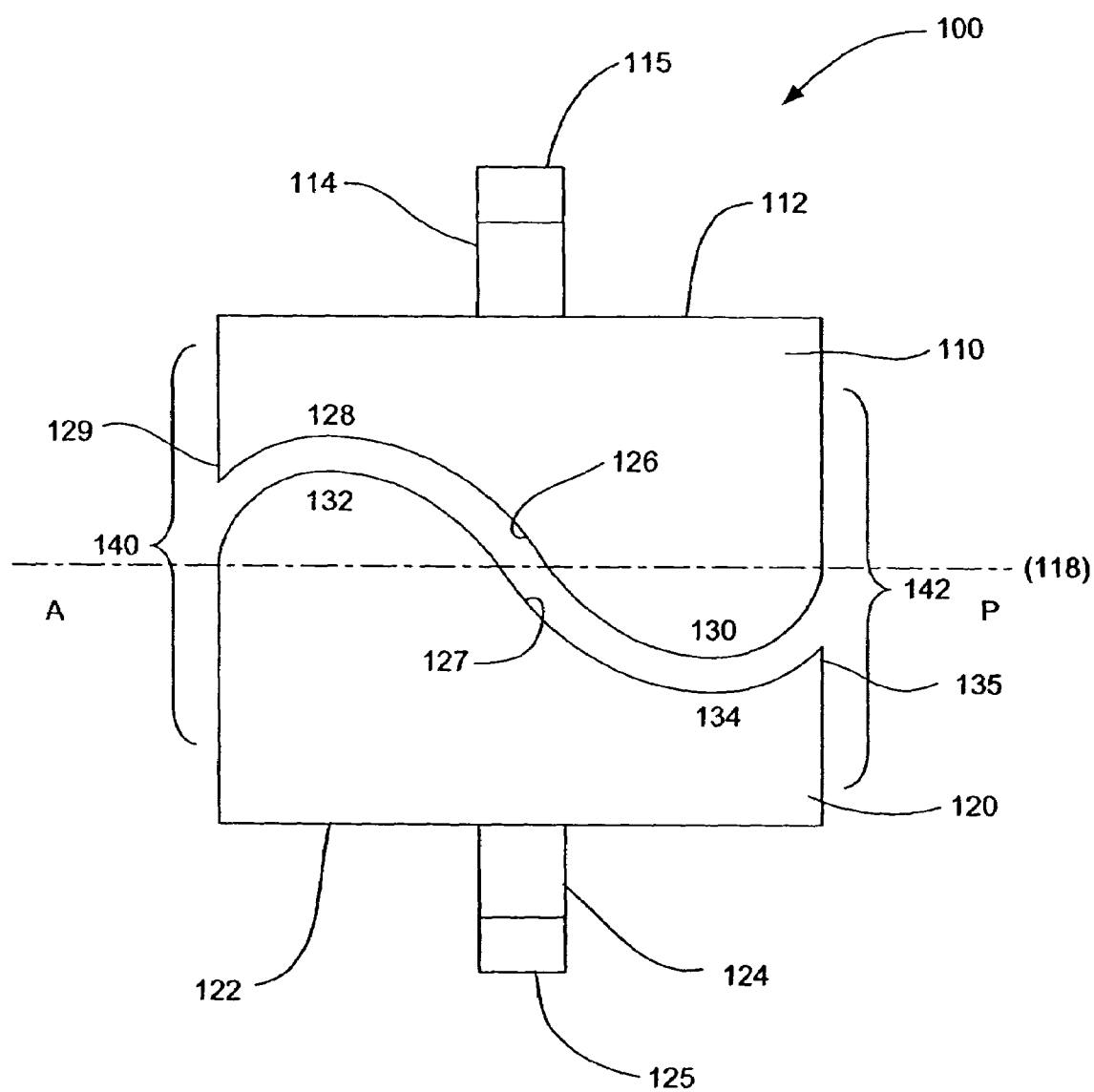
FIG. 1 is a side view of an embodiment of the disclosed implant of the invention which is designed for surgical insertion from a lateral approach. The keels depicted in this embodiment are oriented perpendicular to the sagittal plane of the spine upon implantation.
Figure 2:
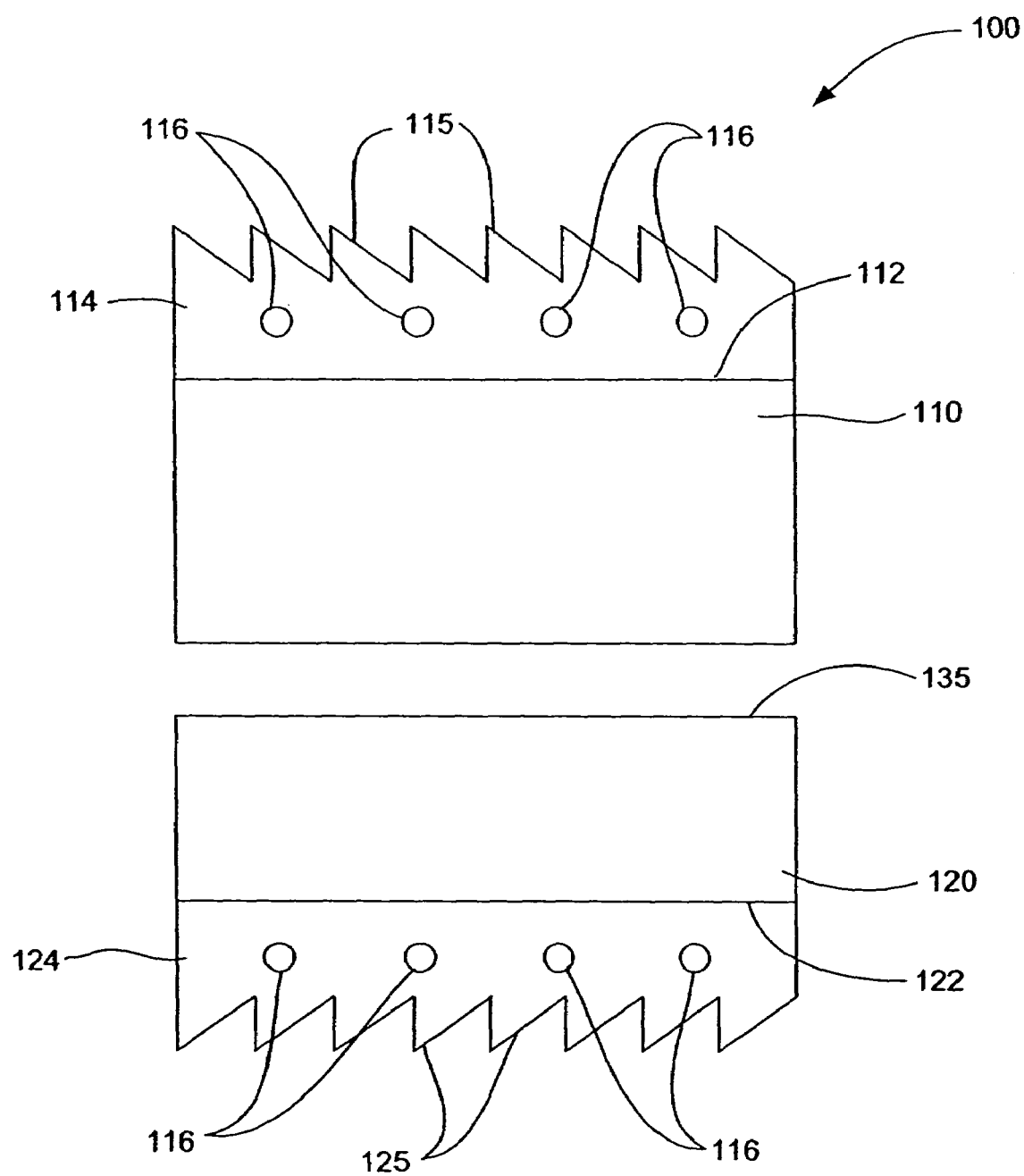
FIG. 2 is an anterior view of the embodiment of the disclosed implant of the invention depicted in FIG. 1.
Figure 3:
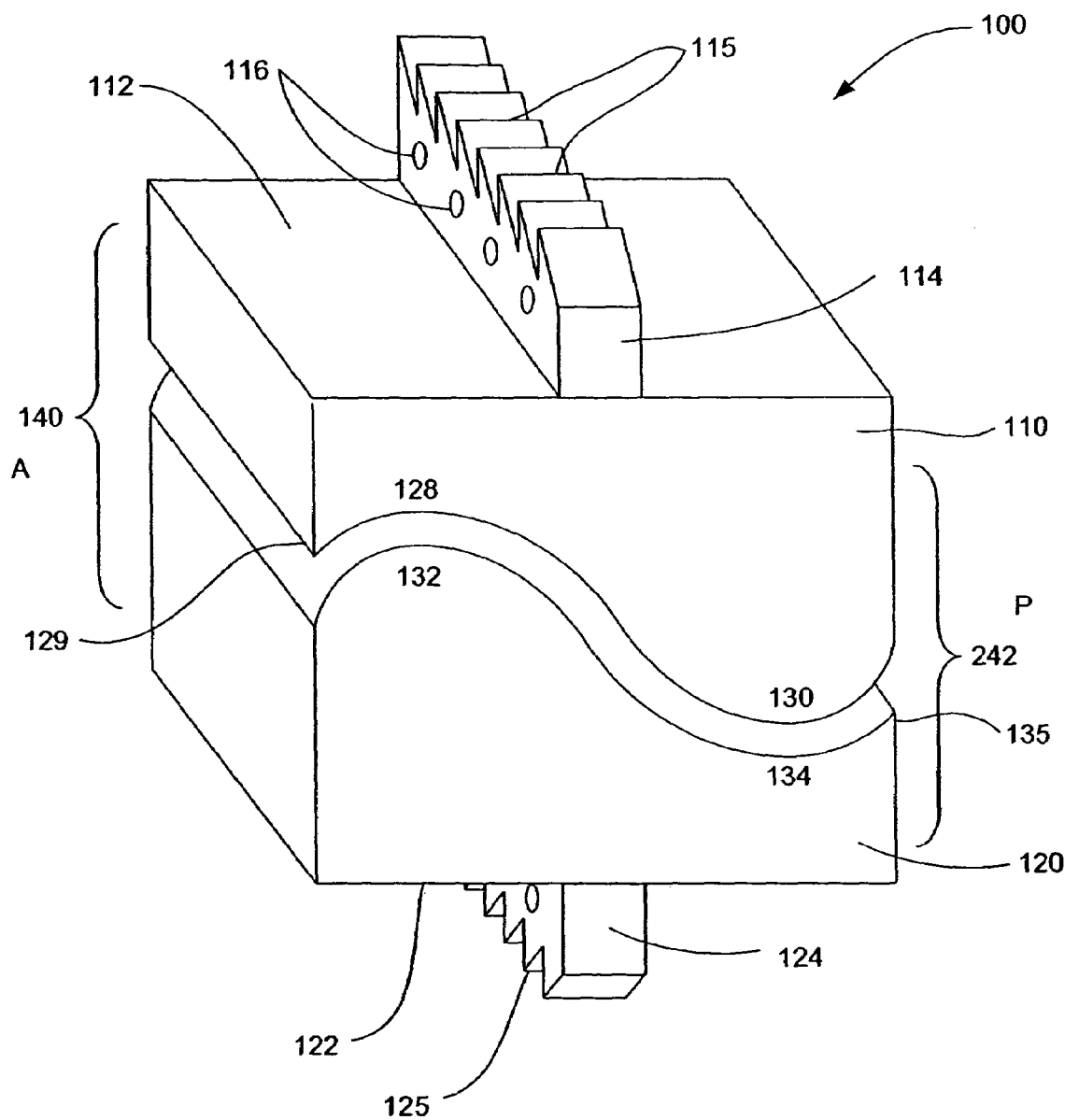
FIG. 3 is a perspective view of the embodiment of the implant of the invention depicted in FIG. 1.

The following description is presented to enable any person skilled in the art to make and use what is disclosed. Various modifications to the embodiments described will be readily apparent to those skilled in the art, and the principles defined herein can be applied to other embodiments and applications without departing from the spirit and scope of what is disclosed and defined by the appended claims. Thus, what is disclosed is not intended to be limited to the embodiments shown, but is to be accorded the widest scope consistent with the principles and features disclosed herein. To the extent necessary to achieve a complete understanding of what is disclosed herein, the specification and drawings of all patents and patent applications cited in this application are incorporated herein by reference.

FIGS. 1-4 show an embodiment of the implant 100 of the invention having a two-piece configuration. The designations, "A" for anterior, "P" for posterior, "RL" for right lateral, and "LL" for left lateral are given in the drawings for spatial orientation. These designations give the relationship of all faces of embodiments of the disclosed intervertebral implant from the superior perspective; i.e. looking down the axis of the spine.

Figure 4:
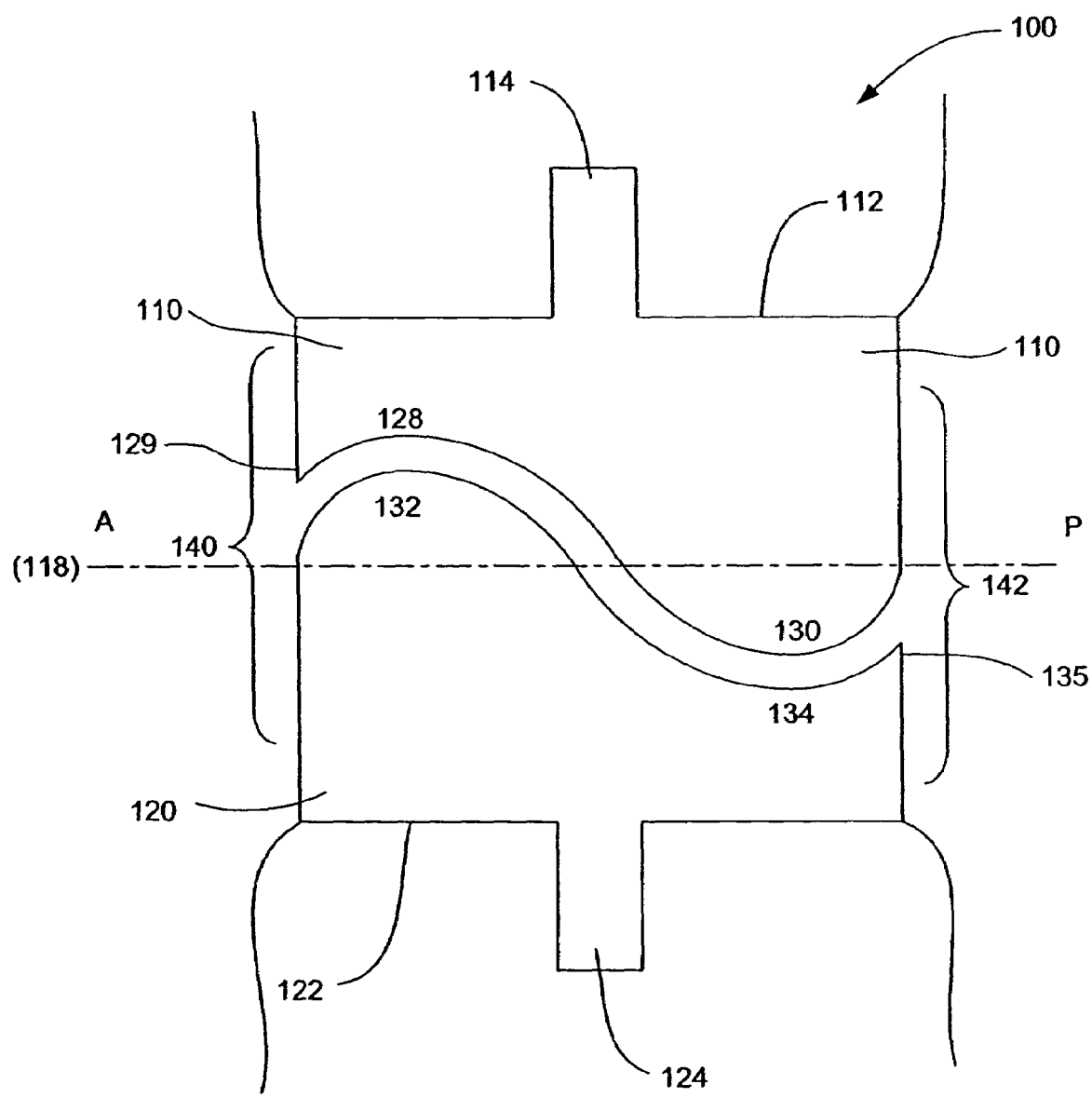
FIG. 4 is a side view of the embodiment of the disclosed implant of the invention depicted in FIG. 1, shown implanted between adjacent vertebrae.
Figure 5:
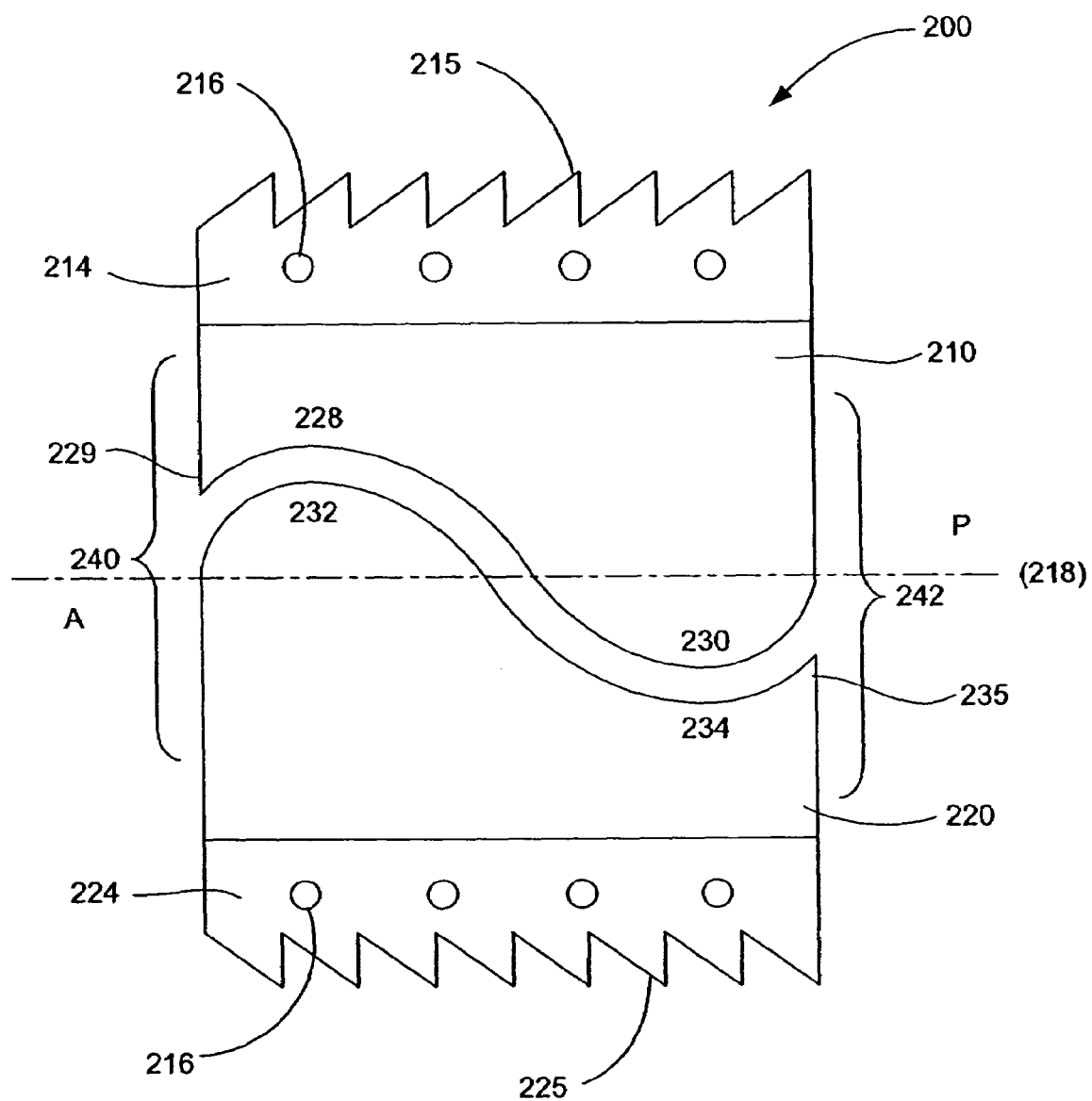
FIG. 5 is a side view of a further embodiment of the disclosed implant of the invention, designed for surgical implantation from an anterior or lateral approach.
Figure 6:
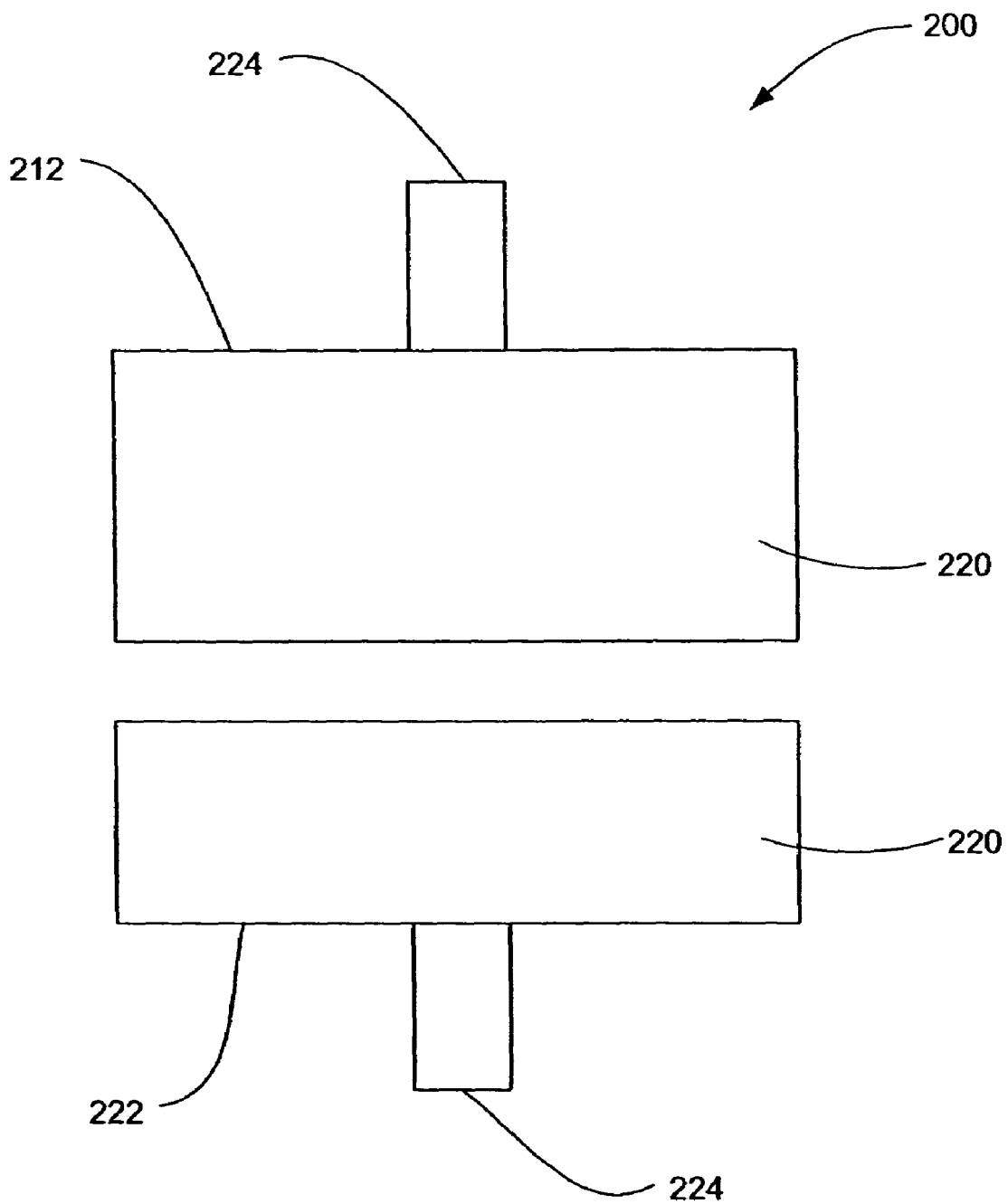
FIG. 6 is an anterior view of the embodiment of the disclosed implant of the invention depicted in FIG. 5.
Figure 7:
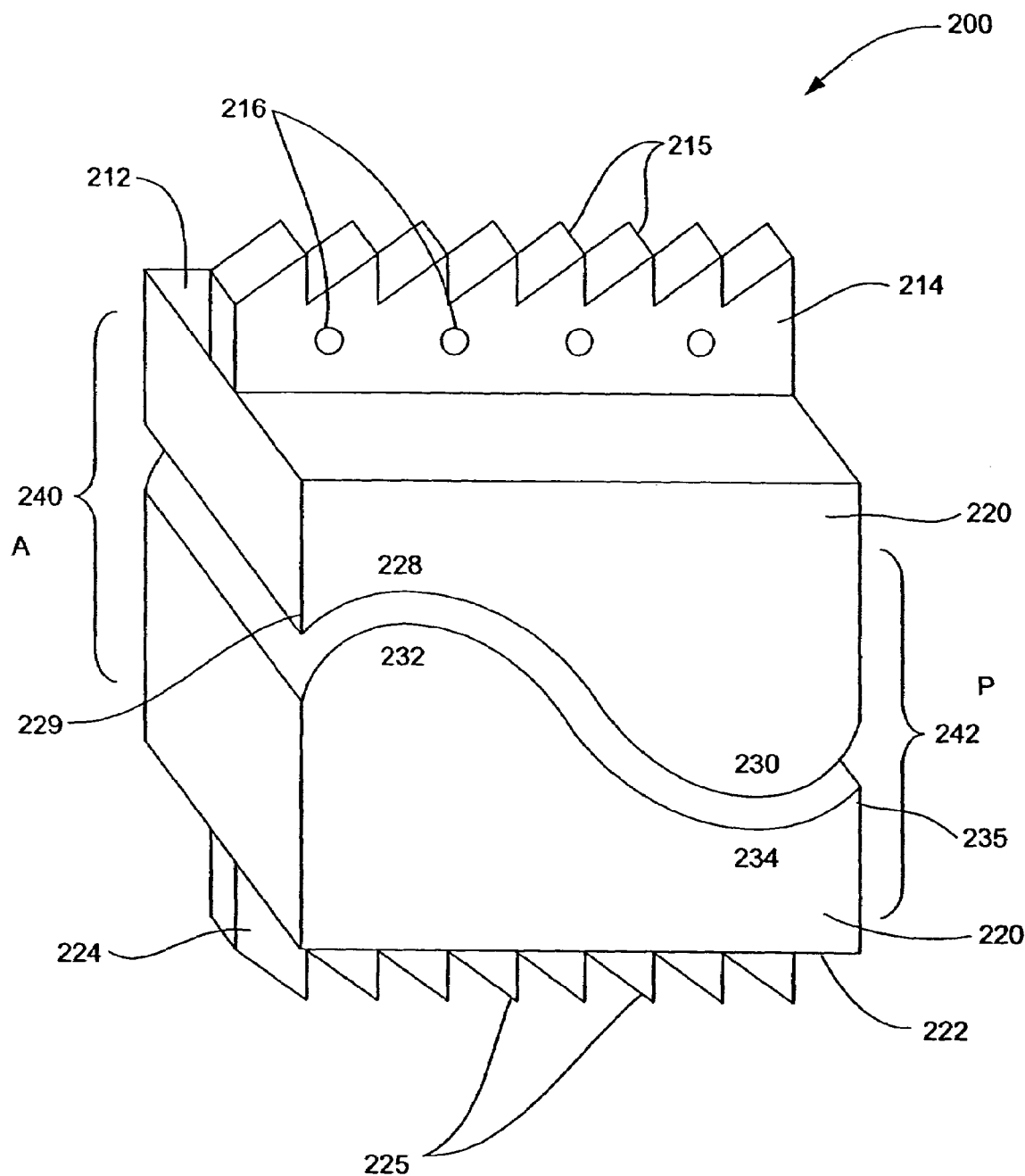
FIG. 7 is a perspective view of the embodiment of the disclosed implant of the invention depicted in FIG. 5.

The implant 100 has a first endplate, or upper endplate 110 that is configured to mate with a first upper vertebral body. The upper endplate 110 of implant 100 has a first exterior surface 112 from which a first keel 114 extends with a first set of teeth 115. The first keel 114 is substantially perpendicular to the median sagittal plane of the spine, in which extension and flexion occur. The first keel 114 in this orientation offers substantial stability during extension and flexion for the implant 100 inserted between the vertebrae of a patient. When the implant 100 is inserted and positioned between two vertebrae, as depicted in FIG. 4, the first exterior surface 112 abuts the first vertebral body. The first keel 114 extends into the cancellous bone of the upper vertebral body, in which a keel-receiving channel has been cut to receive the first keel 114, to anchor implant 100 into position. The first keel 114 also can have a plurality of apertures 116 through it, to enhance bone ingrowth from the first vertebral body and stabilization of the implant.

The implant 100 also has a second, or lower, endplate 120 that is configured to mate with a second, lower vertebral body. The lower endplate 120 has a second exterior surface 122 from which a keel 124 extends with a second set of teeth 125. As with the first endplate 110 and first keel 114, the second exterior surface 122 abuts the second vertebral body when the implant 100 is implanted, and the second keel 124 extends into the cancellous bone of the second vertebral body within a keel-receiving channel cut to receive the second keel 124. The second keel 124 thus anchors the implant 100 and stabilizes the spine. The second keel 124 extending from the second exterior surface 122 can have a plurality of apertures 116 through the second keel 124 to promote bone ingrowth and further stabilize the anchored implant 100. The second keel 124, like the first keel 114, is also perpendicular to the median sagittal plane of the spine, in which extension and flexion occur.

As noted above, the upper endplate 110 of implant 100 has a first exterior surface 112 from which a first keel 114 extends with a first set of teeth 115. In one embodiment, when implant 100 is inserted between vertebrae, the first keel 114 extends across the first exterior surface 112, about perpendicular to the sagittal plane of the spine and about perpendicular to the anterior-posterior axis 118 of the implant 100. In another embodiment, the first keel 114 extends only partially across the first exterior surface 112, about perpendicular to the sagittal plane of the spine and the anterior-posterior axis 118 of the implant 100. It will be appreciated that a plurality of first keels 114 extending from the first exterior surface 112 and oriented along the axis 118 is also contemplated by this disclosure.

Likewise, the lower endplate 120 has a second exterior surface 122 from which a keel 124 extends with a second set of teeth 125. In one embodiment, when implant 100 is inserted between vertebrae, the second keel 124 is about perpendicular to the sagittal plane of the spine. As described above for the first upper endplate 110, in one embodiment, the second keel 124 extends across the second exterior surface 122, while in another embodiment, the second keel 124 extends partially across the second exterior surface 122. It will be appreciated that a plurality of second keels 124 extending from the second exterior surface 122 is also contemplated by this disclosure.

The teeth 115, 125 further serve to anchor the implant and prevent expulsion or displacement after the implant 100 is surgically positioned. The teeth 115, 125 of the keels 114, 124 point towards the left lateral face of implant 100 when the embodiment is inserted into a keel-receiving channel cut into a vertebral body from the left lateral approach to the spine.

This orientation assists in keeping the implant in place as its teeth block backward motion of the implant along the line of implantation. This orientation is shown in the figures, and is particularly evident where the second keel 124 is fully displayed, as in FIG. 2, for example, which provides an anterior view of implant 100. Alternatively, the teeth 115, 125 point towards the right lateral face of implant 100 when the embodiments are inserted into a keel-receiving channel cut into a vertebral body from the right lateral approach to the spine.

The inner surface 126 of the first (upper) endplate 110 and inner surface 127 of the second (lower) endplate 120 oppose each other when the implant 100 is implanted. The opposition of the two inner surfaces 126 and 127 aligns two articulating elements 140, 142 along the antero-posterior axis 118 of the implant 100 to allow flexion and extension of the spine, as well as limited lateral and rotational movement. The first articulating element 140 is an anterior articulating element, and the second articulating element 142 is a posterior articulating element. Each articulating element 140, 142 includes two units, with a first unit which can be formed from or connected with one of the inner surfaces 126, 127 and a second unit which can be formed from or connected with the other of the inner surfaces 126, 127.

The specific configuration of the inner surfaces 126, 127 of the endplates 110, 120 of the implant 100 can be as follows. The first inner surface 126 of the upper endplate 110 can have a sigmoidal or S-shaped curve that is continuous and smooth all along the curve.

The S-shape creates contours of the first inner surface 126. The S-shape of the first inner surface 126 creates a first projection 130 and a first depression 128 aligned along an anterior-posterior axis. In two different embodiments, the first depression 128 can be located anteriorly and the first projection 130 can be located posteriorly or, the first depression 128 can be located posteriorly and the first projection 130 can be positioned anteriorly. Preferably the depression 128 is located anterior and the projection 130 is located posterior to more closely model flexion and extension of the spine. Accordingly, during flexion or forward bending, the anterior articulation element 140 is able to model such forward motion. The posterior articulating element 142 can spread apart. During extension or backward bending, the posterior articulating element 142 is able to model such backward motion. The anterior articulating element 140 can spread apart. The exterior edge (either anterior or posterior, depending upon the placement of the depression) of the first depression 128 includes first peak 129 adapted to prevent slippage during movement of the opposing and mating second projection on the second inner surface 127, discussed in greater detail below.

The second inner surface 127 also is S-shaped and continuous and smooth along the curve. The S-shape of the second inner surface 127 is inverted with respect to the S-shape of the first inner surface 126, and adapted to mate with the curve of the first inner surface 126.

The inverted S-shape likewise bestows contours to the second inner surface 127. The inverted S-shape of the second inner surface 127 creates a second projection 132 and a second depression 134, aligned next to each other on an anterior-posterior axis 118. In two different embodiments, the second projection 132 can be positioned anteriorly with the second depression 134 positioned posteriorly, or the second projection 132 can be positioned posteriorly with the second depression 134 located anteriorly. An exterior edge (either anterior or posterior, depending upon the placement of the depression) of the second depression 134 includes a peak 135 adapted to prevent slippage during movement of the opposing and mating first projection 130. Thus, the two depressions 128, 134 have peaks 129, 135 that serve as stops to prevent over-rotation of the two endplates 110, 120 relative to each other. The ligaments and anatomy of the spine further constrain the mobility of the implant.

As noted above, the second projection 132 from the second endplate 120 mates with the first depression 128 from the first endplate 110 to permit a smooth rolling motion. The mating combination of the second projection 132 with the first depression 128 is a first articulating element 140. The first projection 130 from the first endplate 110 mates with the second depression 134 from the second endplate 120 to permit a smooth rolling motion. The mating combination of the first projection 130 and the second depression 134 is a second articulating element 142. The two articulating elements 140, 142 are joined in continuous smooth fashion in an anterior-posterior plane, so that the endplates 110, 120 translate motion about a pivot point, which motion creates forward flexion and rearward extension of the spine. The smooth surfaces and continuous contours further allow for some lateral and rotational movement of the spine.

When implant 100 is inserted between vertebrae from a lateral approach, the first and second keels 114, 124 are aligned in the axial plane, perpendicular to the sagittal plane of the vertebrae. The first and second keels 114, 124 extend into the vertebral bodies to anchor implant 100 into position, and are perpendicular to the median sagittal plane of the spine, in which extension and flexion occur. The first and second keels 114, 124 in this orientation offer substantial stability during extension and flexion for implant 100 inserted between the vertebrae of a patient. Additionally, the first and second keels 114, 124 in this embodiment are aligned with and support the axis of articulation of implant 100 defined by an RL to LL orientation.

As noted above, in the embodiment shown in FIGS. 1-4, the first and second keels 114, 124 include apertures 116 that facilitate bone ingrowth. For example, bone from the vertebral bodies can grow through the apertures 116 and aid in securing the first and second keels 114, 124 and thereby also aid in securing implant 100 once inserted between adjacent vertebral bodies. In addition, surfaces defined by the first and second keels 114, 124 and the first and second exterior surfaces 112, 122 of implant 100 can be roughened in order to promote bone ingrowth into these defined surfaces of implant 100. In other embodiments the apertures 116, the first and second keels 114, 124, and the first and second exterior surfaces 112,122 of implant 100 can be coated with materials that promote bone growth such as for example bone morphogenic protein, BMP, or structural materials such as hyaluronic acid, HA, or other substance which promotes growth of bone relative to and into the keels 114, 124, keel apertures 116, and other external surfaces of the implant 100.

The disclosure of the implant of the invention further contemplates treating the exterior surfaces 112, 122, including the keels 114, 124, to create a porous surface and thereby promote bone ingrowth and fixation. One such treatment can be with plasma spray titanium, and another, with a coating of sintered beads. Alternatively, the implant 100 can have casted porous surfaces, where the porous surface is integral to the implant 100.

Figure 8A:
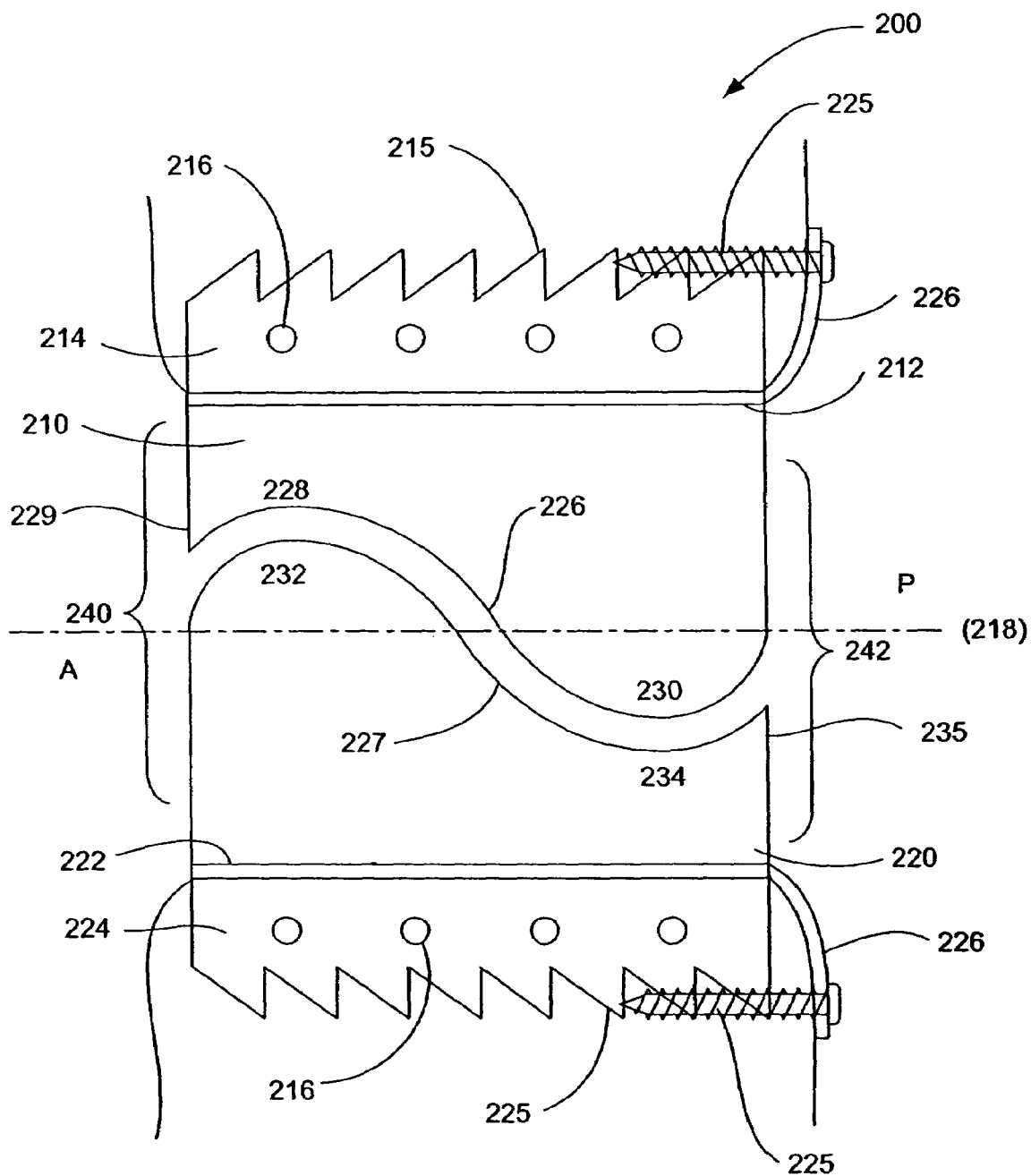
FIG. 8A is a side view of the embodiment of the disclosed implant of the invention depicted in FIG. 5, shown implanted between two adjacent vertebrae and anchored by keels and bone screws.

The disclosure also contemplates the use of bone screws, as depicted in FIG. 8A or other appropriate bone anchor, to anchor the implant 100. Such bone screws 225 or anchors can be applied through a bore hole in each of the first and second endplates 210, 220 and into the vertebral bodies in which the first and second endplates 210, 220 are embedded. The bore hole can be defined by a lip on each of the first endplate 210 and the second end 220 plate. The lip 226 wraps partially over each vertebral body and places the bore hold (not shown) over the vertebral body so that the bone screw 225 or other bone anchor can further anchor the implant 200 to the vertebral body.

Figure 8B:
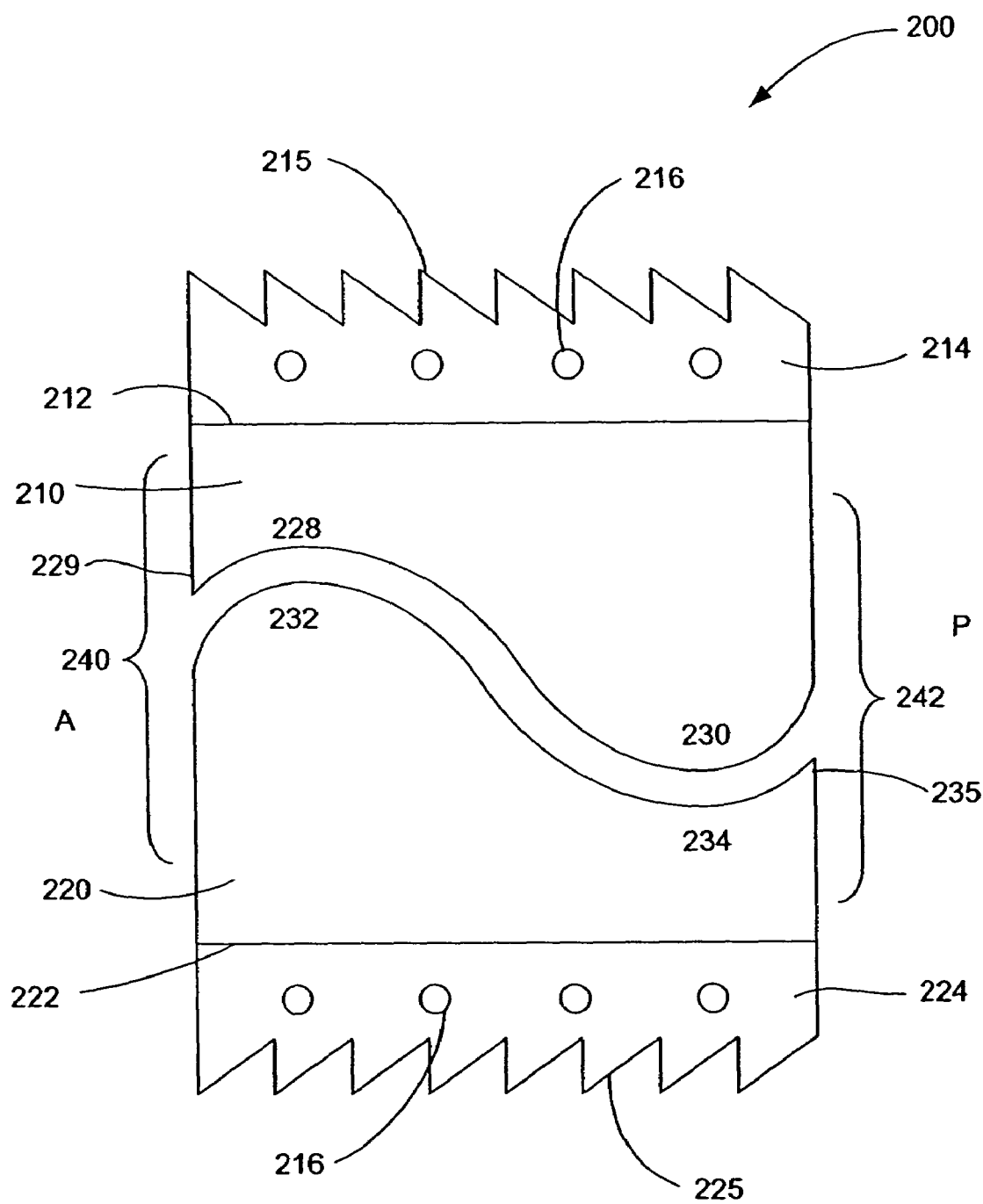
FIG. 8B is a side view of the embodiment of the disclosed implant of the invention with the teeth of the keels intended for implantation from the anterior, i.e., from a direction opposite that of the implant depicted in FIG. 8A.

FIGS. 5-8B. Implant 200 is a further embodiment of the invention. Implant 200 is intended for implantation using a posterior surgical approach (FIGS. 7, 8a, e.g.), or posterolateral surgical approach (FIG. 8b, e.g.).

As with the implant 100, implant 200 has a first endplate, or upper endplate 210 that is configured to mate with a first vertebra. The upper endplate 210 of implant 200 has a first exterior surface 212 from which a first keel 214 extends with a first set of teeth 215. Implant 200 also has a second endplate, or lower endplate 220 that is configured to mate with a second vertebra. The lower endplate 220 has a second exterior surface 222 from which a keel 224 extends with a second set of teeth 225.

When positioned between adjacent vertebrae, the first exterior surface 212 of the implant 200 abuts the vertebral body. In this embodiment for surgical insertion from an anterior approach or posterior approach, when implant 200 is inserted between vertebrae, the first keel 214 extends longitudinally across the first exterior surface 212, about parallel to the median sagittal plane of the spine, the plane in which extension and flexion occur. This is in contrast to implant 100, wherein the keel 114 extends across the first exterior surface 112 in a plane that is substantially perpendicular to the sagittal plane of the vertebrae, and parallel to the axial plane of the vertebrae. It should be appreciated that the first keel 214 of implant 200 also can extend only partially across the first exterior surface 212, about parallel to the sagittal plane of the spine. It also will be appreciated that a plurality of keels is further contemplated by this disclosure.

When the implant 200 is inserted between adjacent vertebrae, the keel 214 is received into a keel-receiving channel. If the implantation uses an anterior surgical approach, then the keel-receiving channel is cut into the vertebral body from an anterior approach. If the implantation surgery uses a posterior approach, then the keel-receiving channel is cut from posterior approach. The resulting keel-receiving channel in either surgical approach is parallel to the sagittal plane of the spine. Note that if the surgical approach were lateral, then the keel-receiving channels would be cut from the left or right lateral side to the opposite side, the keel-receiving channels would perpendicular to the sagittal plane of the spine, and implant 100 should be used.

Teeth 215 on the keel 214 prevent displacement or expulsion of the implant 200, and also serve as anchors. The teeth 215 on the keel 214, whether the keel 214 extends fully or partially across the first exterior surface 212 of the upper endplate 210, point anteriorly when the embodiment is to be inserted from an anterior to posterior direction. This orientation is shown in the figures, and is particularly evident where the keel 214 is fully displayed, as in FIGS. 5 and 7, for example. The teeth 215 on the keel 214 point posteriorly when the embodiment is to be inserted from a posterior to anterior direction (see FIG. 8b).

The lower endplate 220 of implant 200 has a second exterior surface 222 from which a keel 224 extends with a second set of teeth 225. When implanted, exterior surface 222 abuts the lower vertebra. In this embodiment, when implant 200 is inserted between vertebrae from either an anterior or posterior approach, the second keel 224 is received into a keel-receiving channel cut into the lower vertebra about parallel to the sagittal plane of the spine. As described above for the first upper endplate 210, the second keel 224 extends longitudinally across the second exterior surface 222, but it can extend partially, rather than fully. As above, it will be appreciated that a plurality of keels is also contemplated by this disclosure.

The second set of teeth 225 of the second keel 224 point towards the anterior for this embodiment that is to be implanted from an anterior approach. The keel 224 is to be received into a keel-receiving channel cut into a vertebral body from an anterior approach to the spine, and the teeth 215 are intended to prevent displacement. This orientation is shown in the figures, and is particularly evident where the second keel 124 is fully displayed, as in FIG. 5 and 7, for example. Alternatively, when the implant 200 is received into position from a posterior surgical approach (see FIG. 8b), the teeth 225 point posteriorly to prevent expulsion of the implant 200 or displacement. The keel 224 is received into a keel-receiving channel cut into the lower vertebra from a posterior approach.

In the embodiment shown in FIGS. 5-8b, the first and second keels 214, 224 include apertures 216 to facilitate bone ingrowth. As described above, surfaces defined by the first and second keels 214, 224 and the first and second exterior surfaces 212, 222 of implant 200 also can be roughened in order to promote bone ingrowth into these defined surfaces of implant 200. In other embodiments the apertures 216, the first and second keels 214, 224, and the first and second exterior surfaces 212, 222 of implant 200 can be coated with materials that promote bone growth.

The disclosure of the implant of the invention further contemplates treating the exterior surfaces 212, 222, including the keels 214, 224, to create a porous surface and thereby promote bone ingrowth and fixation. One such treatment can be with plasma spray titanium, and another, with a coating of sintered beads. Alternatively, the implant 200 can have casted porous surfaces, where the porous surface is integral to the implant 200.

The disclosure of the implant of the invention also contemplates the use of bone screws 225 or other appropriate bone anchor as in FIG. 8a. Such bone screws 225 or anchors can be applied through a bore hole in each of the first and second endplates 210, 220 and into the vertebral bodies in which the first and second endplates 210, 220 are embedded. The bore hole can be defined by a lip on each of the first endplate 210 and the second end 220 plate. The lip 226 wraps partially over each vertebral body and places the bore hold (not shown) over the vertebral body so that the bone screw 225 or other bone anchor can further anchor the implant 200 to the vertebral body.

The inner surface 226 of the first (upper) endplate 210 and inner surface 227 of the second (lower) endplate 220 oppose each other when the implant 200 is implanted. The opposition of the two inner surfaces 226 and 227 aligns two articulating elements 240, 242 along the anterior axis 218 of the implant 200 to allow flexion and extension of the spine, as well as limited lateral and rotational movement. Each articulating element 240, 242 includes a projection derived from either the first or second inner surface 226, 227, and a depression derived from the other of the first or second inner surface 226, 227 as described in greater detail below.

The specific configuration of the articulating elements 240, 242 can operate essentially as described for the articulating elements 140, 142 of implant 100. The first inner surface 226 of the upper endplate 210 can have a sigmoidal or S-shaped curve that is continuous and smooth all along the curve.

The S-shape creates contours of the first inner surface 226. The S-shape of the first inner surface 226 creates a first projection 230 and a first depression 228 aligned in along an anterior-posterior axis. In two different embodiments, the first depression 228 can be located anteriorly and the first projection 230 can be located posteriorly or, the first depression 228 can be located posteriorly and the first projection 230 can be positioned anteriorly. Preferably the depression 228 is located anterior and the projection 230 is located posterior to more closely model flexion and extension of the spine. Accordingly, during flexion in forward bending, the anterior articulation element 240 is able to model such forward motion. The posterior articulating element 242 can spread apart. During extension and backward bending, the posterior articulating element 242 is able to model such backward motion. The anterior articulating element 240 can spread apart. The first depression 228 has an exterior edge (either anterior or posterior, depending upon the placement of the depression) that includes a peak 229 adapted to prevent slippage during movement of the opposing and mating second projection on the second inner surface 227, discussed in greater detail below.

The second inner surface 227 also is S-shaped and continuous and smooth along the curve. The S-shape of the second inner surface 227 is inverted with respect to the S-shape of the first inner surface 226, and adapted to mate with the curve of the first inner surface 226.

The inverted S-shape likewise bestows contours to the second inner surface 227. The inverted S-shape of the second inner surface 227 creates a second projection 232 and a second depression 234, aligned next to each other on an anterior-posterior axis 218. In two different embodiments, the second projection 232 can be positioned anteriorly with the second depression 234 positioned posteriorly, or the second projection 232 can be positioned posteriorly with the second depression 234 located anteriorly. The second depression 234 has an exterior edge (either anterior or posterior, depending upon the placement of the depression) that includes a peak 235 adapted to prevent slippage during movement of the opposing and mating first projection 230. Thus, the two depressions 228, 234 have peaks 229, 235 that serve as stops to prevent over-rotation of the two endplates 210, 220 relative to each other. The ligaments and anatomy of the spine further constrain the mobility of the implant.

As noted above, the second projection 232 from the second endplate 220 mates with the first depression 228 from the first endplate 210 to permit a smooth rolling motion. The mating combination of the second projection 232 with the first depression 228 is a first articulating element 240. The first projection 230 from the first endplate 210 mates with the second depression 234 from the second endplate 220 to permit a smooth rolling motion. The mating combination of the first projection 230 and the second depression 234 is a second articulating element 242. The two articulating elements 240, 242 are joined in continuous smooth fashion in an anterior-posterior plane, so that the endplates 210, 220 translate motion about a pivot point, which motion creates forward flexion and rearward extension of the spine. The smooth surfaces and continuous contours further allow for some lateral and rotational movement of the spine.

Figure 9A:
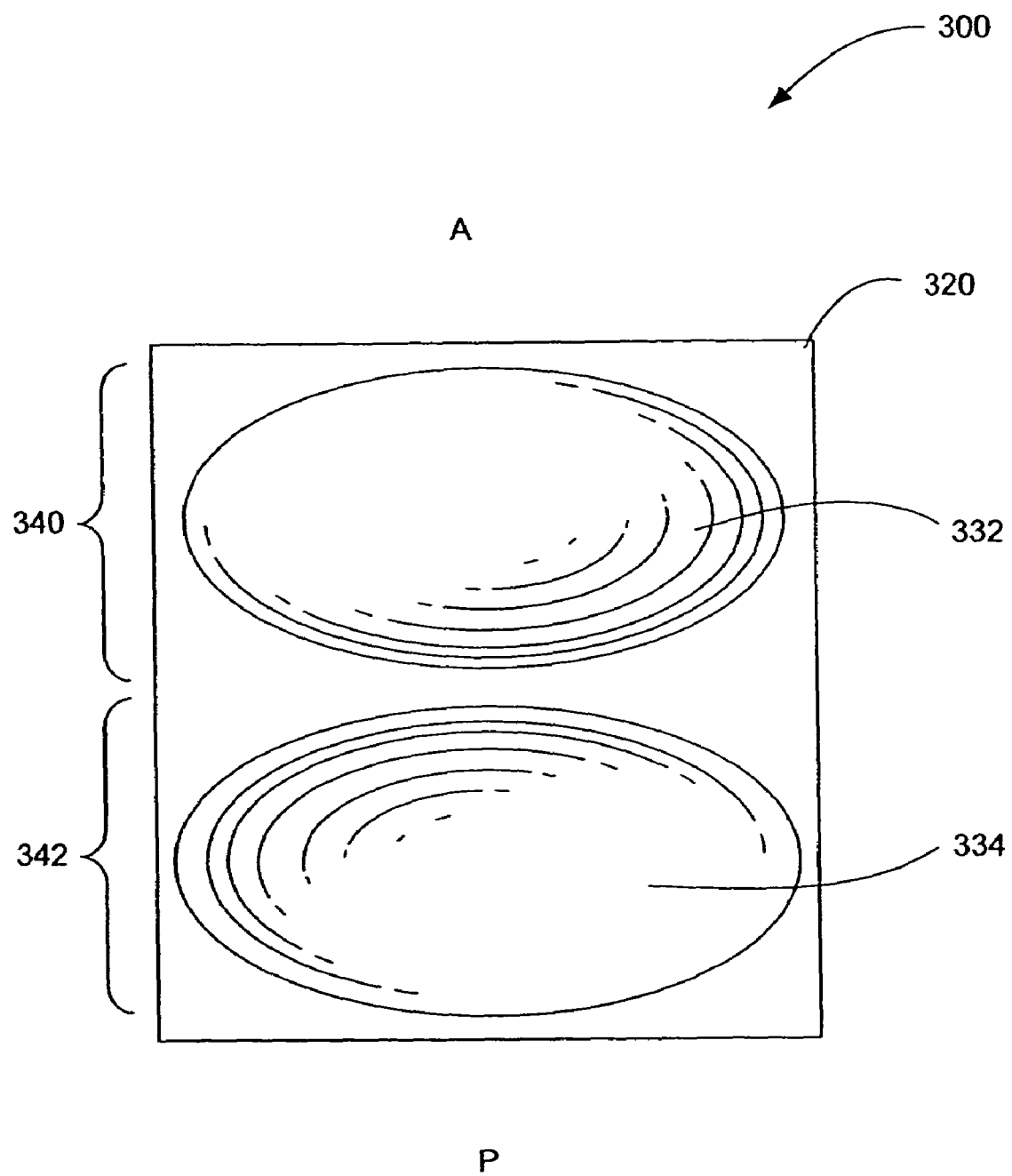
FIG. 9A is a top view of a lower endplate of a further embodiment of the disclosed implant of the invention.
Figure 9B:
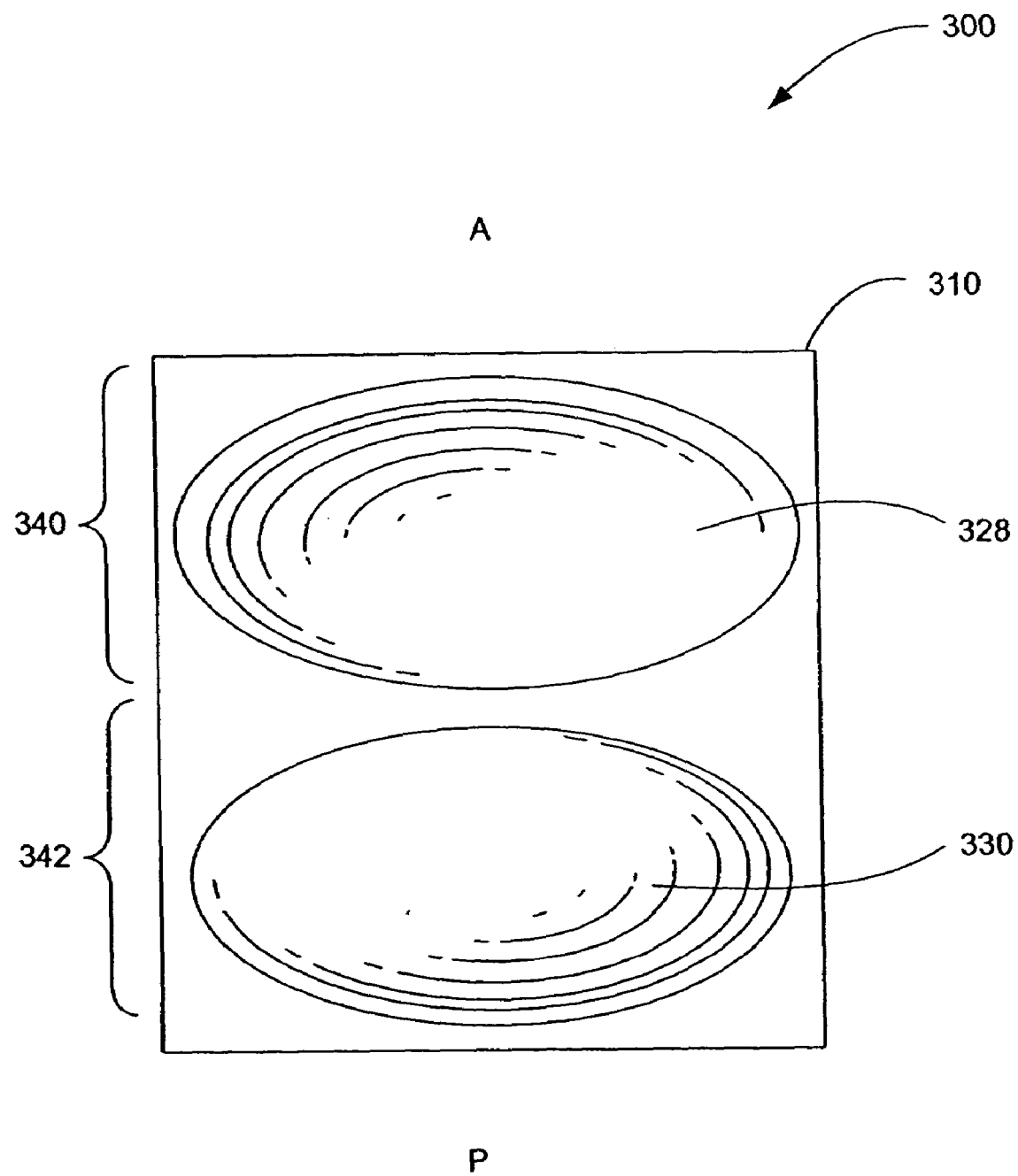
FIG. 9B is a top view of an upper endplate of the embodiment of the disclosed implant of the invention depicted in FIG. 9A.
Figure 9C:
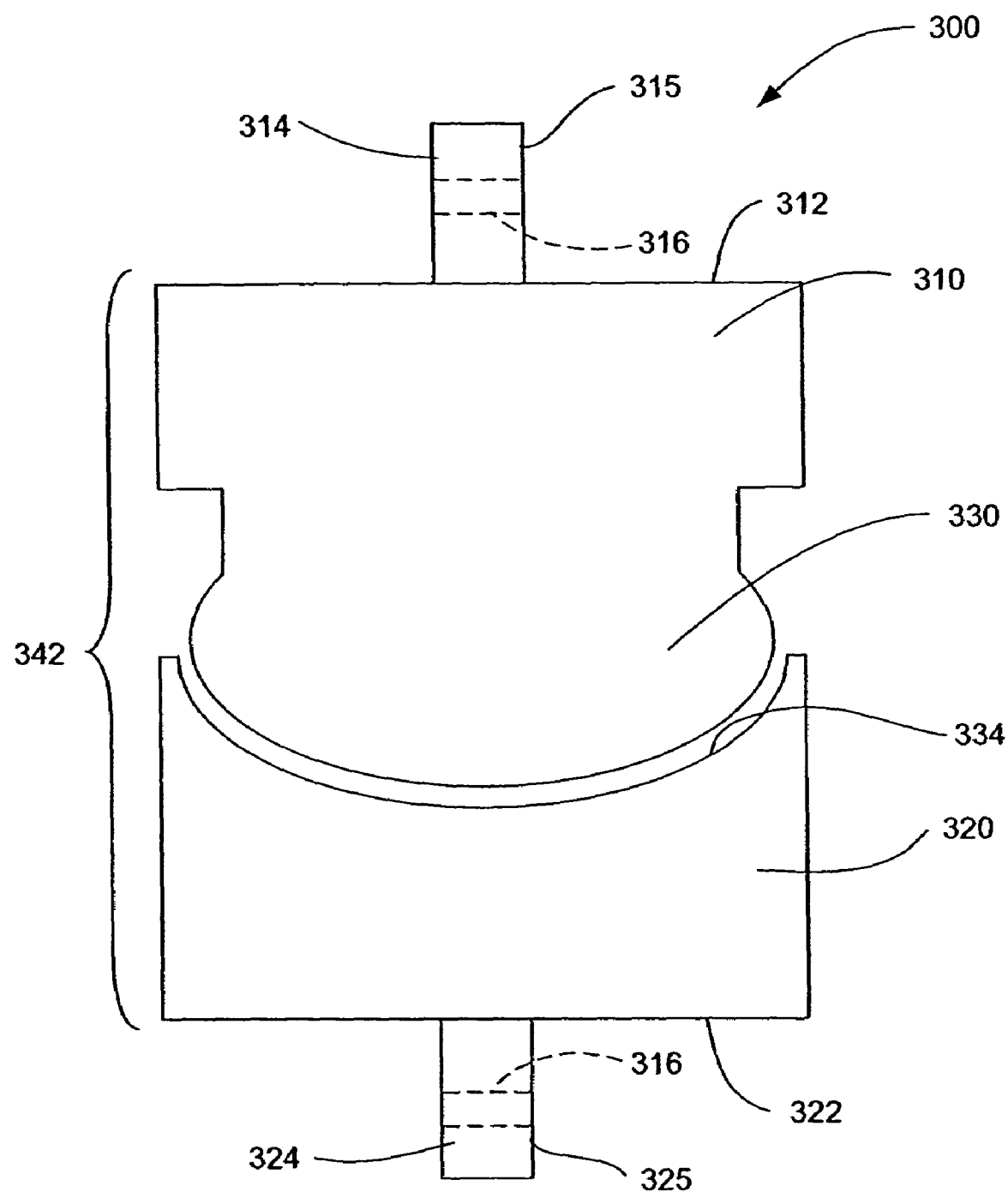
FIG. 9C is a posterior view of the embodiment of the disclosed implant of the invention depicted in FIGS. 9A and 9B.
Figure 10A:
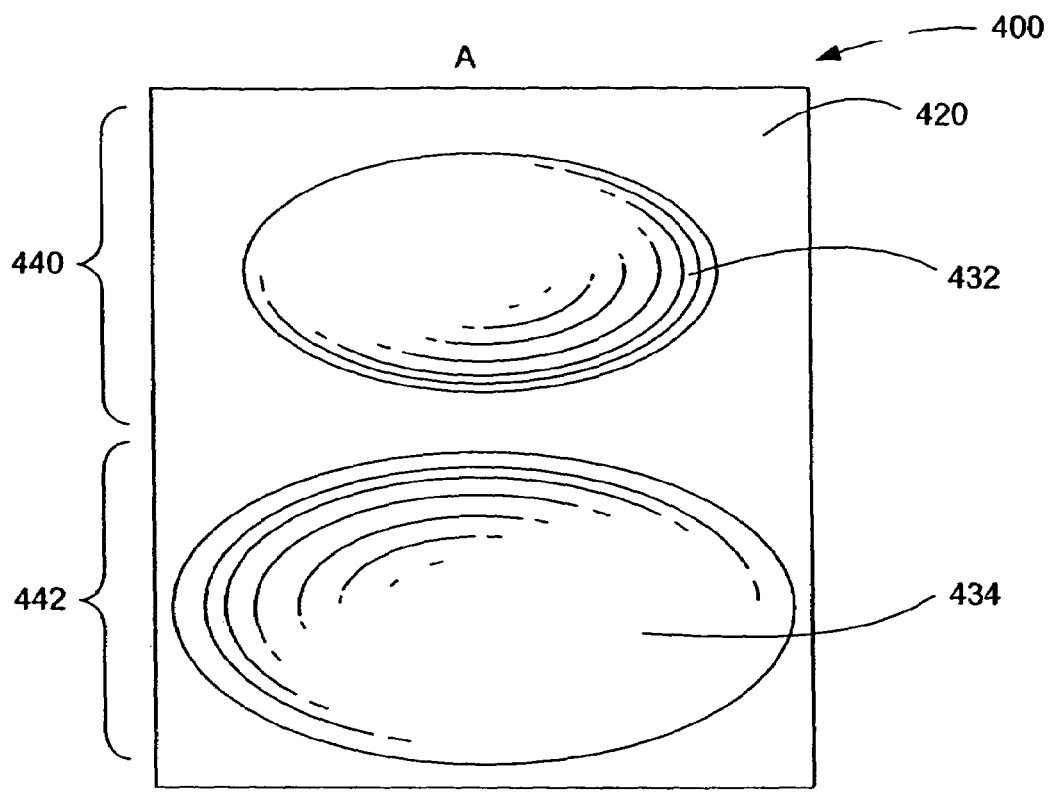
FIG. 10A is a top view of a lower endplate of a further embodiment of the implant of the disclosed invention.
Figure 10B:
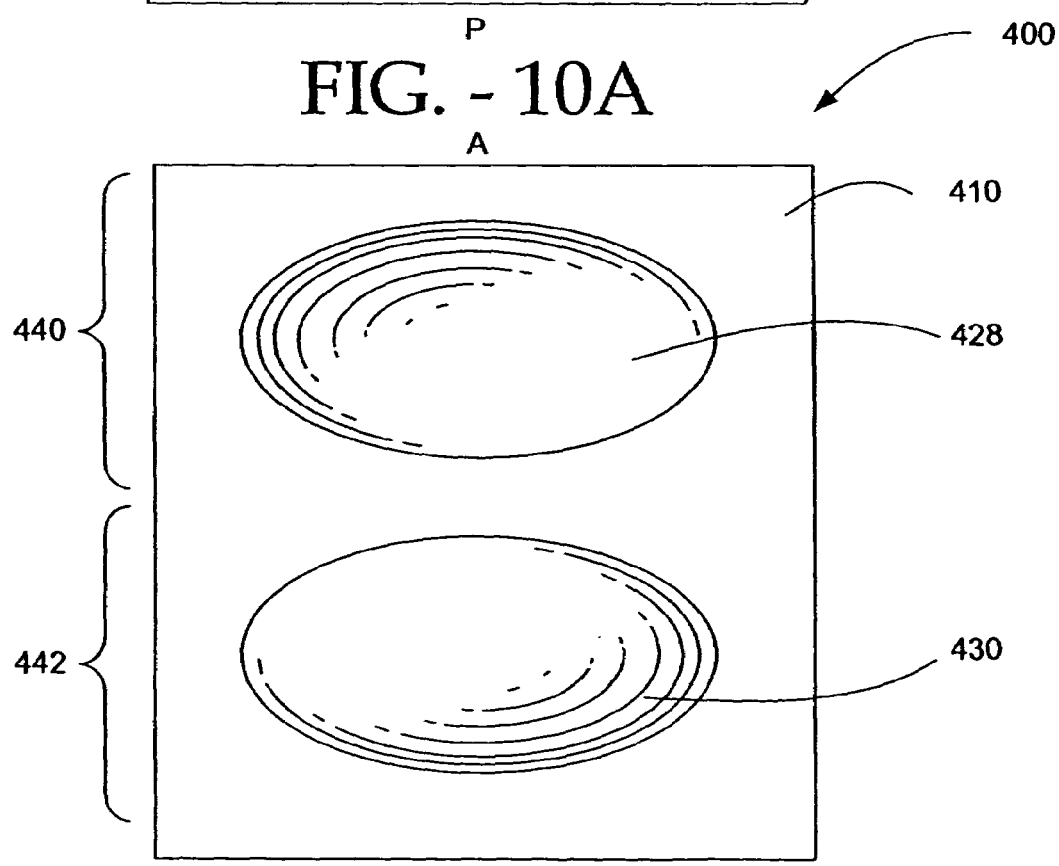
FIG. 10B is a top view of an upper endplate of the embodiment of the implant of the disclosed invention depicted in FIG. 10A.
Figure 10C:
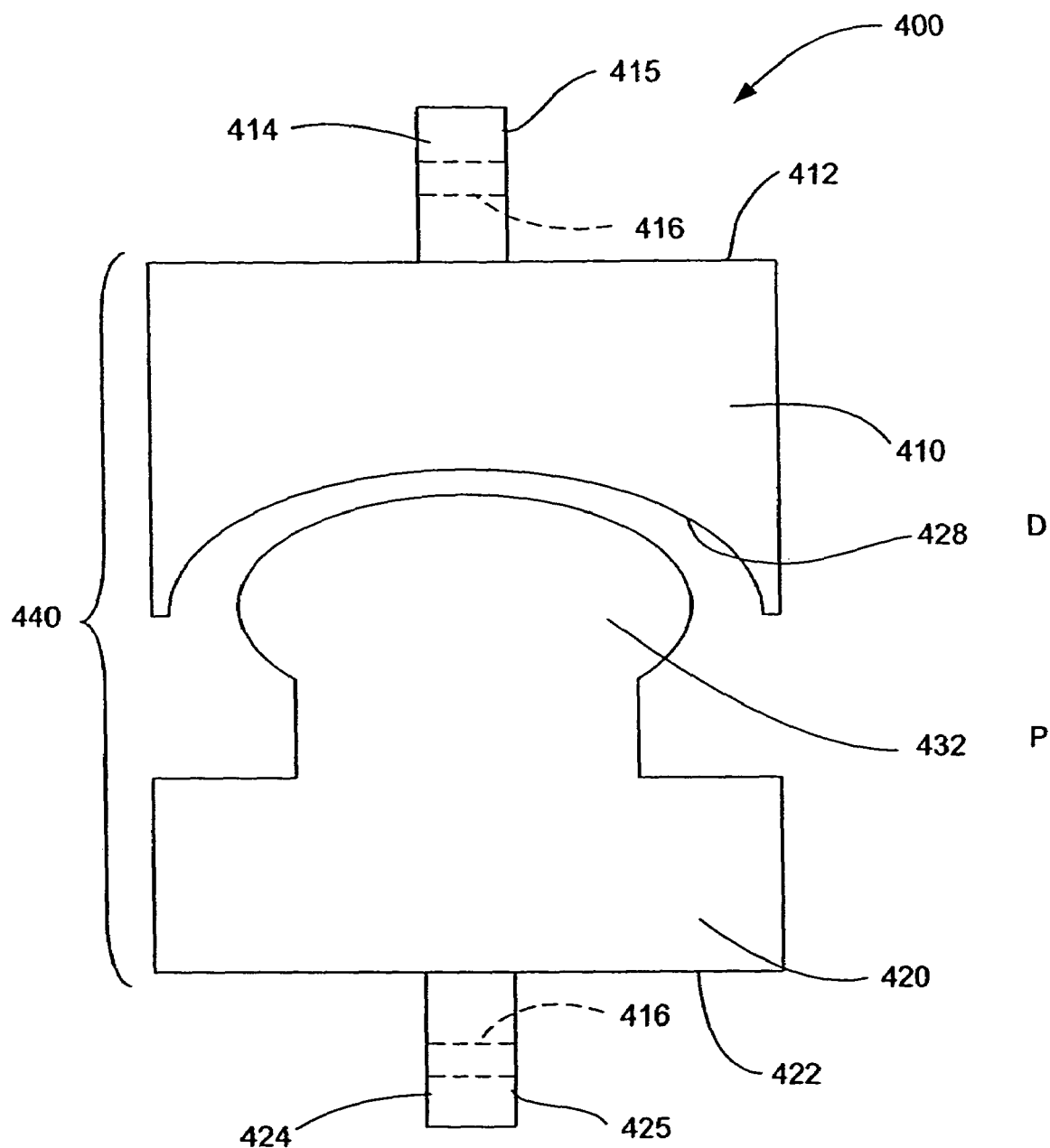
FIG. 10C is an anterior view of the embodiment of the implant of the disclosed invention depicted in FIGS. 10A and 10B.
Figure 10D:
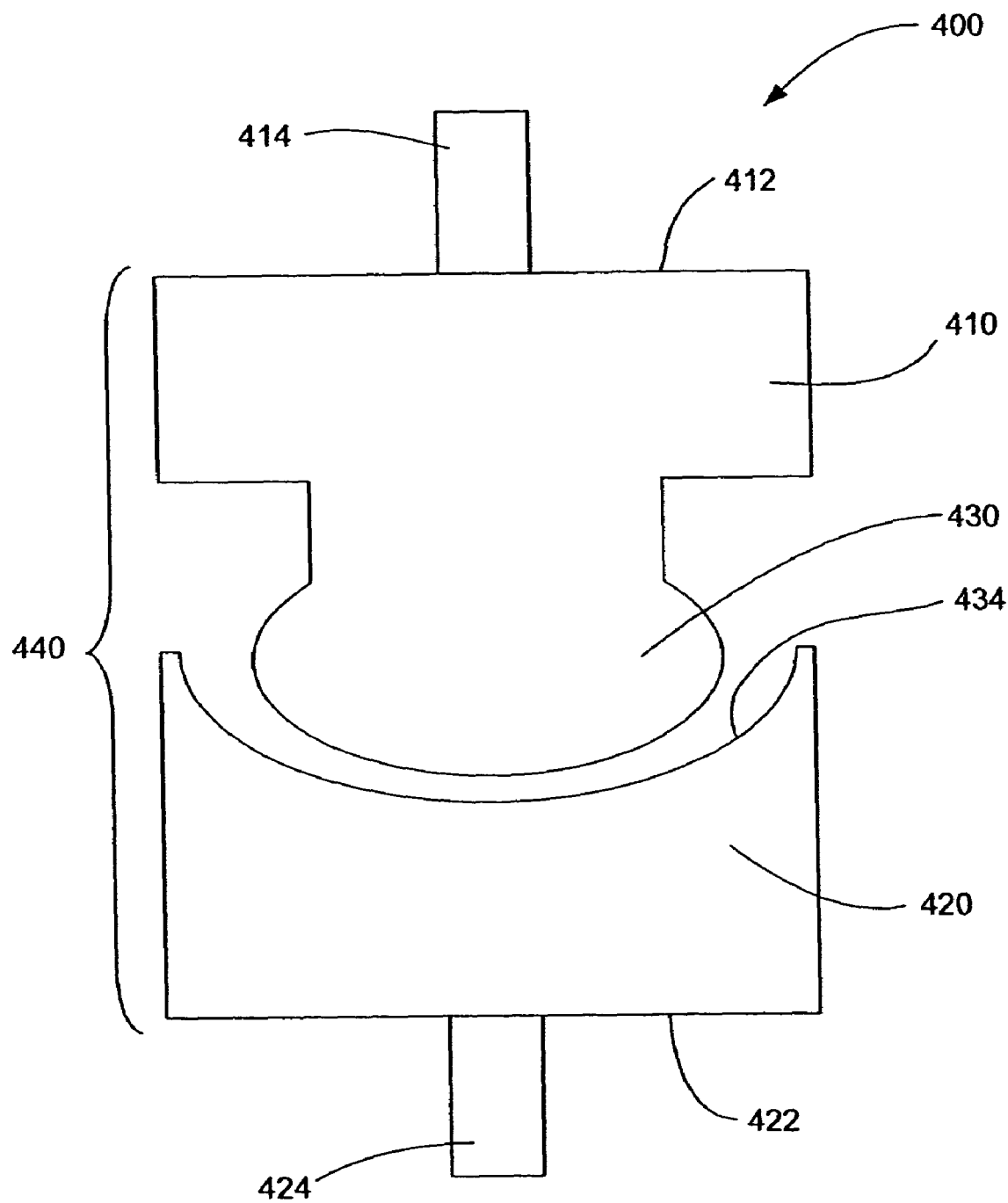
FIG. 10D is a posterior view of the embodiment of the implant of the disclosed invention depicted in FIGS. 10A, 10B, and 10C.

Another embodiment 300, depicted in FIGS. 9A-9C, has a first exterior surface 312, second exterior surface 322, first keel 314, and second keel 324 substantially similar to the corresponding parts disclosed above for embodiments 100 and 200. That is, embodiment 300 has a first upper endplate 310 that mates with a first upper vertebral body. The first upper endplate 310 has a first exterior surface 312 from which a first keel 314 extends. First keel 314 has a first set of teeth 315. The first keel 314 can be substantially perpendicular to the sagittal plate of the spine, where implant 300 is intended and designed to be inserted from a lateral direction. Alternatively, the first keel 314 can be substantially parallel to the sagittal plane of the spine where the implant 300 is intended to be implanted posteriorly or anteriorly.

When the implant 300 is inserted and positioned between two vertebral bodies, the first exterior surface 312 abuts the first vertebral body. The first keel 314 extends into the cancellous bone of the upper vertebral body, in which a keel-receiving channel has been cut to receive the first keel 314, to anchor the implant 300 in position. The first keel 314 can have a plurality of apertures 316 (not shown) through it, to enhance bone ingrowth from the first vertebral body and stabilization of the implant 300.

The implant 300 also has a second lower endplate 320, that is configured to mate with a second lower vertebral body. The lower endplate 320 has a second exterior surface 322 from which a second keel 324 extends with a second set of teeth 325. As with the first endplate 310, and first keel 314, the second exterior surface 322 abuts the second vertebral body when the implant 300 is implanted, and the second keel 324 extends into the cancellous bone of the second vertebral body within a keel-receiving channel that is cut to receive the second keel 324. The second keel 324 thus anchors the implant 300 and stabilizes the spine. The second keel 324 extending from the second exterior surface 322 can have a plurality of apertures 316 to promote bone ingrowth and further stabilize the anchored implant 300. The second keel 324, like the first keel 314, is also perpendicular to the median sagittal plane of the spine. Alternatively, like the first keel 314, the second keel 324 can be substantially parallel to the sagittal plane of the spine where the implant 300 is intended to be implanted posteriorly or anteriorly.

In one embodiment, when implant 300 is inserted laterally between two vertebral bodies, the first keel 314 and second keel 324 extend fully across the first exterior surfaces 312, 322 about perpendicular to the sagittal plane of the spine and about perpendicular to the anterior-posterior axis 318 of the implant 300. In another embodiment, the first keel 314 and second keel 324 extend only partially across the first exterior surface 312 and second exterior surface 322, about perpendicular to the sagittal plane of the spine and the anterior-posterior axis 318 of the implant 300. It will be appreciated that a plurality of first keels 314 extending from the first exterior surface 312, and a plurality of second keels 324 extending from the second exterior surface 322 and oriented along the axis 118 are also contemplated by this disclosure.

Alternatively, an anterior-posterior approach can be used to implant the implant 300. In that case, keels 312 and 324, or a plurality of keels 312 and 324, can be oriented parallel to the sagittal plane of the spine.

As with the other embodiments already disclosed, the teeth 315, 325 further serve to anchor the implant 300 and prevent expulsion or displacement after the implant 300 is surgically positioned. The teeth 315, 325 of the keels 314, 324 point towards the left lateral face of the implant 300 when the embodiment is inserted into a keel-receiving channel cut into a vertebral body from the left lateral approach to the spine. Alternatively, the teeth 315, 325 point towards the right lateral face of the implant 300 when the embodiment is inserted into a keel-receiving channel cut into a vertebral body from the right lateral approach to the spine.

While the exterior surfaces and keels of embodiment 300 are substantially similar to corresponding parts of embodiments 100 and 200, embodiment 300 has inner surfaces that differ. In the embodiments 100 and 200, the projections and depressions are substantially cylindrical which allows for the rolling articulation for extension and flexion. Such arrangements allow for lateral and side-to-side slipping. If desired, the cylindrical projections and depressions can be curved at the lateral edge in order to enhance lateral or side-to-side slippage. In embodiment 300, the first and second articulating elements 340, 342 can comprise a ball-and-socket type of interaction by altering somewhat the form of their first and second depressions 328, 334 and first and second projections 330, 332 of a substantially hemispherical shape. The union of each depression 328, 334 with a compatible hemispherical projection 330, 332 should be sufficiently loose to allow for forward-rearward motion that is translated in implant 300 as flexion and extension of the spine. Each articulating element 340, 342 is also sufficiently flexible and loose as to permit rotational and lateral movement of the spine. Free rotational and lateral movement is still restricted by the ligaments associated with the spine. It should be appreciated by one of skill in the art that ball-and-socket type of articulating element need not have hemispherical projections extending from the inner surface but rather, can have any other shape that allows pivoting to occur.

A further embodiment 400 is depicted in FIGS. 10A-10D. In embodiment 400, like embodiment 300, has ball-and-socket type first and second articulating elements 440 and 442 aligned along an anterior axis. However, in embodiment 400, the articulating element 442 has a looser fit than the anterior articulating element 440. That is, the depression 434 is substantially broader than the second projection 430 that mates with it. In contrast, the anterior articulating element 440 has a relatively tighter fit. The depression 428 loosely fits the projection 432, but not as loosely as the fit of the posterior articulating element 442. This preferred embodiment allows extension and flexion and greater twisting about the anterior articulating element 440. This configuration can increase flexibility of the spine for flexion and extension, rotational movement, and lateral bending.

One of ordinary skill in the art will appreciate that it is further within the scope of this disclosure to have an anterior articulating element 440 that has a looser fit than the posterior articulating element 442. In such case, the depression 428 is substantially broader than the projection 432 that mates with it, while the depression 434 of the posterior articulating element 442 has a relatively tighter fit with the projection 430.

As with the other implants disclosed above, embodiment 400 has a first exterior surface 412, second exterior surface 422, first keel 414, and second keel 424. That is, embodiment 400 has a first upper endplate 410 that mates with a first upper vertebral body. The first upper endplate 410 has a first exterior surface 412 from which a first keel 414 extends. First keel 414 has a first set of teeth 415. The first keel 414 can be substantially perpendicular to the sagittal plate of the spine, where implant 400 is intended and designed to be inserted from a lateral direction. Alternatively, the first keel 414 can be substantially parallel to the sagittal plane of the spine where the implant 400 is intended to be implanted posteriorly or anteriorly.

When the implant 400 is inserted and positioned between two vertebral bodies, the first exterior surface 412 abuts the first vertebral body. The first keel 414 extends into the cancellous bone of the upper vertebral body, in which a keel-receiving channel has been cut to receive the first keel 414, to anchor the implant 400 in position. The first keel 414 can have a plurality of apertures 416 through it, to enhance bone ingrowth from the first vertebral body and stabilization of the implant 400.

The implant 400 also has a second lower endplate 420, that is configured to mate with a second lower vertebral body. The lower endplate 420 has a second exterior surface 422 from which a second keel 424 extends with a second set of teeth 425. As with the first endplate 410, and first keel 414, the second exterior surface 422 abuts the second vertebral body when the implant 400 is implanted, and the second keel 424 extends into the cancellous bone of the second vertebral body within a keel-receiving channel that is cut to receive the second keel 424. The second keel 424 thus anchors the implant 400 and stabilizes the spine. The second keel 424 extending from the second exterior surface 422 can have a plurality of apertures 416 to promote bone ingrowth and further stabilize the anchored implant 400. The second keel 424, like the first keel 414, is also perpendicular to the median sagittal plane of the spine. Alternatively, like the first keel 414, the second keel 424 can be substantially parallel to the sagittal plane of the spine where the implant 400 is intended to be implanted postero- or antero- laterally.

In one embodiment, when implant 400 is inserted laterally between two vertebral bodies, the first keel 414 and second keel 424 extend fully across the first exterior surfaces 412, 422 about perpendicular to the sagittal plane of the spine and about perpendicular to the anterior-posterior axis 418 of the implant 400. In another embodiment, the first keel 414 and second keel 424 extend only partially across the first exterior surface 412 and second exterior surface 422, about perpendicular to the sagittal plane of the spine and the antero-posterior axis 418 of the implant 400. It will be appreciated that a plurality of first keels 414 extending from the first exterior surface 412, and a plurality of second keels 424 extending from the second exterior surface 422 and oriented along the axis 418 are also contemplated by this disclosure.

Alternatively, an anterior-posterior approach can be used to implant the implant 400. In that case, keels 412 and 424, or a plurality of keels 412 and 424, can be oriented parallel to the sagittal plane of the spine.

As with the other embodiments already disclosed, the teeth 415, 425 further serve to anchor the implant 400 and prevent expulsion or displacement after the implant 400 is surgically positioned. The teeth 415, 425 of the keels 414, 424 point towards the left lateral face of the implant 400 when the embodiment is inserted into a keel-receiving channel cut into a vertebral body from the left lateral approach to the spine. Alternatively, the teeth 415, 425 point towards the right lateral face of the implant 400 when the embodiment is inserted into a keel-receiving channel cut into a vertebral body from the right lateral approach to the spine.

Any of the implants disclosed above can be made of medical grade titanium, stainless steel, or cobalt chrome. Other materials that have appropriate structural strength and that are suitable for implantation into a patient can also be used.

One class of materials contemplated for use in any of the above implants is the class of biocompatible polymers. Copolymers, blends and composites of polymers are also contemplated for fabrication of parts of the disclosed device. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer.

One group of biocompatible polymers are the polyaryl ester ketones which has several members, which include polyetheretherketone (PEEK), and polyetherketoneketone (PEKK). PEEK has proven as a durable material for implants, as well as meeting criteria of biocompatibility. Medical grade PEEK is available from Victrex Corporation under the product name PEEK-OPTIMA. Medical grade PEKK is available from Oxford Performance Materials under the name OXPEKK, and also from CoorsTek under the name Bio- PEKK. Still another interesting group of biocompatible polymers are polyalkyl biocompatible polymers, such as polyethylenes, polypropylenes, and the like.

These medical grade biocompatible polymers are also available as reinforced polymer materials. To reinforce a polymeric material, fillers, are added to a polymer, copolymer, polymer blend, or polymer composite. Fillers are added to modify properties, such as mechanical, optical, and thermal properties. In this case, fillers, such as carbon fibers, are added to reinforce the polymers mechanically to enhance strength for certain uses, such as load bearing devices.

Figure 11:
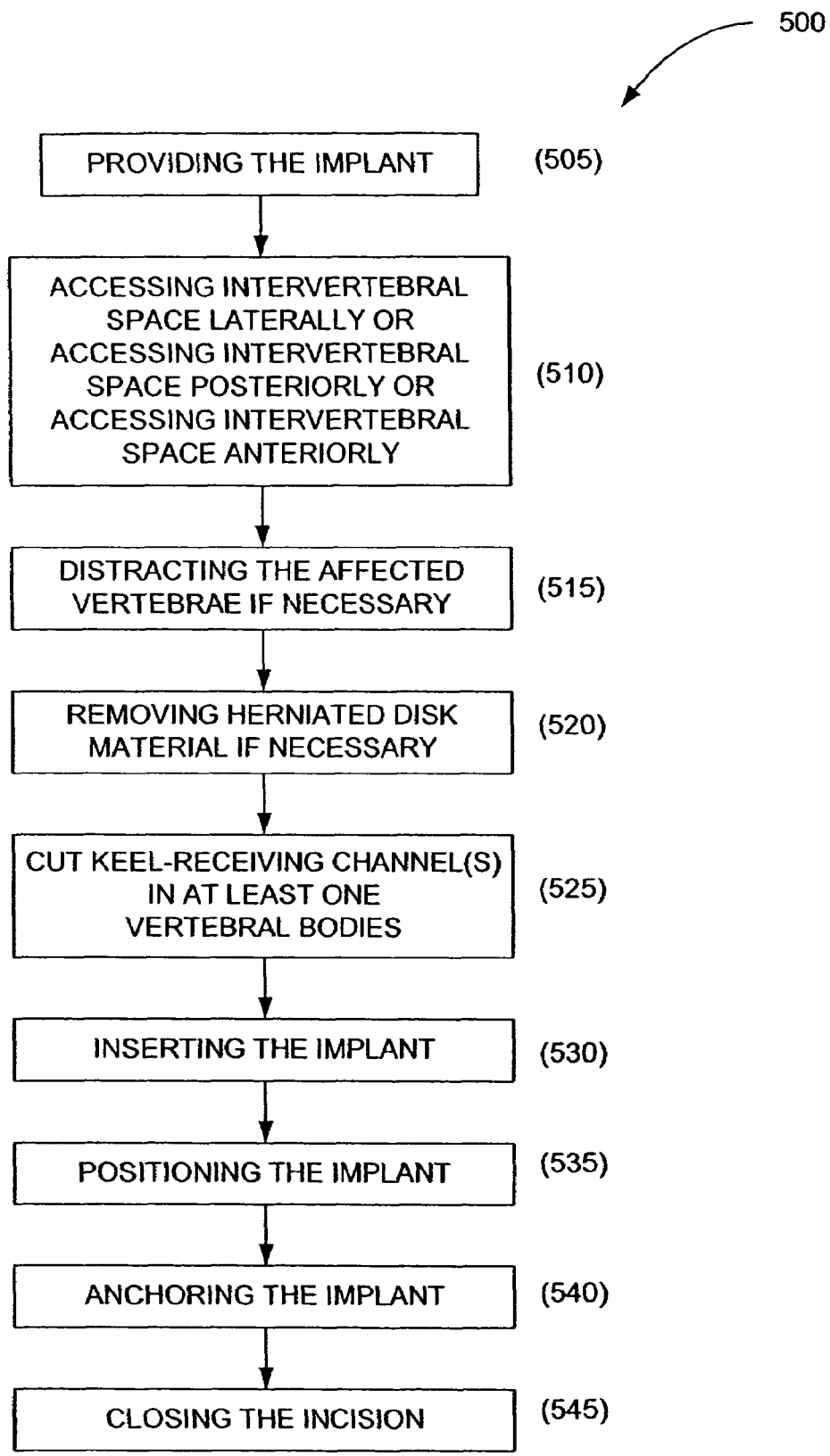
FIG. 11 is a block diagram illustrating the steps of a method for inserting the disclosed embodiments of the implant of the invention between two adjacent vertebral bodies. This method can be adapted for lateral, anterior or posterior surgical approaches.

FIG. 11 is a block diagram showing the basic steps of the method for laterally inserting the implant 100. After providing an implant 505, the spine is exposed through a lateral access 510, and distracted if necessary 515. The intervertebral disk is removed 520, if necessary. The affected vertebrae are distracted, if necessary 520. A tool, such as the one disclosed in application Ser. No. 10/685,134 of James F. Zucherman et al., filed Oct. 14, 2003, and entitled, "Tools for Implanting an Artificial Vertebral Disk and Method," incorporated herein by reference, is inserted laterally between the vertebral bodies and used to cut keel-receiving channels in the vertebral bodies to receive the keels of the implant 525. FIG. 12A depicts a top view of a cutting tool 700 used to prepare the vertebral bodies for the implant 100 and FIG. 12B depicts a side view of tool 700. The cutting tool 700 has a handle 710 at its proximal end for controlling the tool during operation. As will be appreciated by those of skill in the art, the handle 710 can be removable or affixed to the cutting end.

The distal end 702 of the tool 700 is forked to form two prongs or tines 705, 706. The end of each tine 705, 706 has a beveled edge 716 at its distal most end. Each tine 705, 706 also has an inner blade 712 located on an inner upper side and an outer blade 714 located on an outer lower side (shown in FIG. 12C). Preferably the inner blades 712 are coplanar with the surface of the inner side of the tine and the outer blades 714 are coplanar with the outer side of the tine. The inner blades 712 are oriented to cut a space in a first intervertebral body for the first surface keel 116 of the implant and the outer blades 714 are oriented to cut a space in the facing intervertebral body for the second surface keel 126. The orientation of the blades is such that each of the cuts made for the keels of the implant are offset and avoid the nerves in the cauda equina or exiting the cauda equina.

Figure 12C:
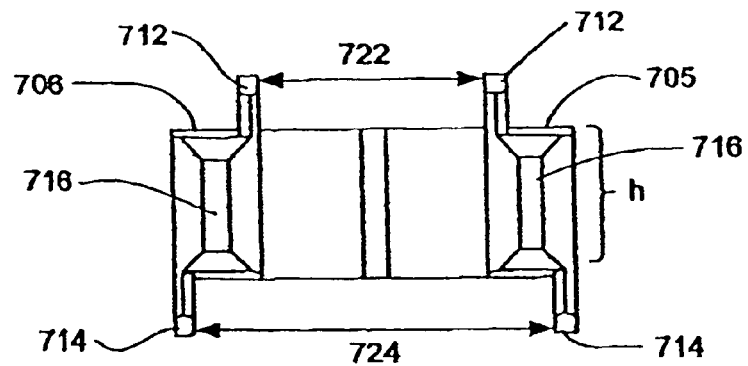
FIG. 12C is a distal end view of an embodiment of the cutting tool of the invention.

FIG. 12C is a view of the distal end of the cutting tool 700 showing the beveled edges 716 of the tines 705, 706 and the inner blades 712 and outer blades 714. The distance 722 between the inner blades 712 is less than the distance 724 between the outer blades and the height h of the tines approximates the distance between two vertebral bodies or the height of the disk space. The blades 712, 714 extend above and below the tines or the height of the tines. As can be seen in FIG. 12C, the beveled sides of the distal end 716 extend and form at least one of the beveled sides of the blades 712, 714.

Figures 12D, 12E:
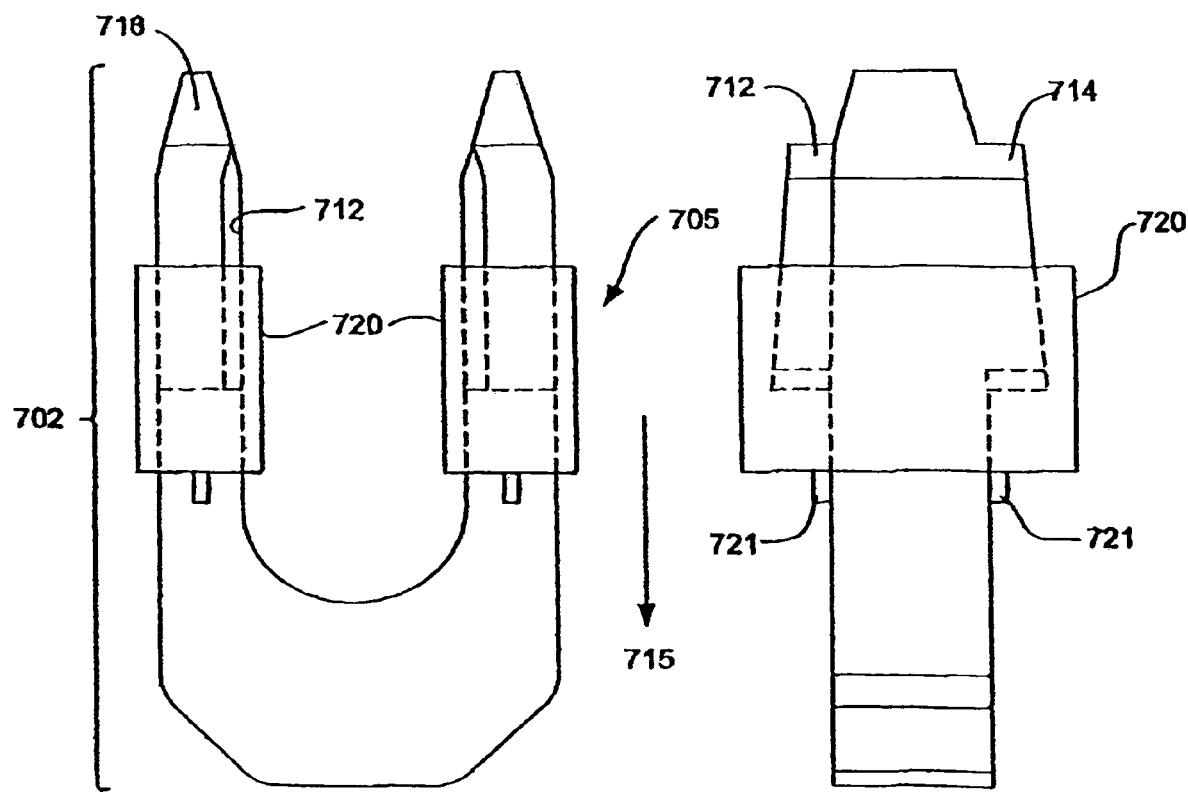
FIG. 12D is a top view of the cutting portion of an alternative embodiment of the cutting tool of the invention showing blade protectors.
FIG. 12E is a side view of the cutting portion of an alternative embodiment of the cutting tool of the invention showing the blade protectors.

FIG. 12D depicts an enlarged top view of the tines 705, 706 of the distal end of cutting tool 700 with the beveled distal edges 716. FIG. 12E is an enlarged side view of the distal end of cutting tool 700. FIGS. 12D and 12E show the retractable blade protector 720 for the blade 712 positioned in a retracted position. As the cutting tool is inserted between vertebral bodies, the retractable blade protector 720 moves in a posterior direction 715 (i.e., toward the handle 710) to expose the inner blade 712 and the outer blade 714 and to enable the blades to cut into the vertebral bodies. These protectors 720 can be spring biased as desired in order to cover the blade 712, 714 as the tool 700 is inserted past the nerves. The protectors 720 are urged in a posterior direction as the blades 712, 714 are urged into the vertebral bodies in order to cut channels for the keels. Springs 721 provide the desired bias to keep the protectors 720 in a forward position covering the blades 712, 718.

As will be appreciated by those of skill in the art, the tool shown in FIG. 12 can be modified such that instead of cutting keel-receiving channels in the upper and lower vertebral bodies at the same time, two tools are provided so that only one vertebral body is cut for keel-receiving channels at a time. For example, a first tool having two tines as described above could be provided having a pair of inner blades located on an upper surface of the tines. A second tool could be provided having tines as described with a pair of outer blades located on the lower surface of the tines. Optionally, the second tool can have a guide corresponding to the location of the first blade on the first tool to ensure that the second cut is optimally aligned with the first cut. In use, a pair of channels can be cut into the upper vertebral body using the first tool. Thereafter a second pair of channels can be cut into the lower vertebral body. Alternate arrangements are also possible, for example, where the first tool has a pair of outer blades and the second tool has a pair of inner blades, or where the first tool has upper and lower blades on a first tine (e.g., right tine) and the second tool has upper and lower blades on a second tine (e.g., left tine).

Figures 13A, 13B:
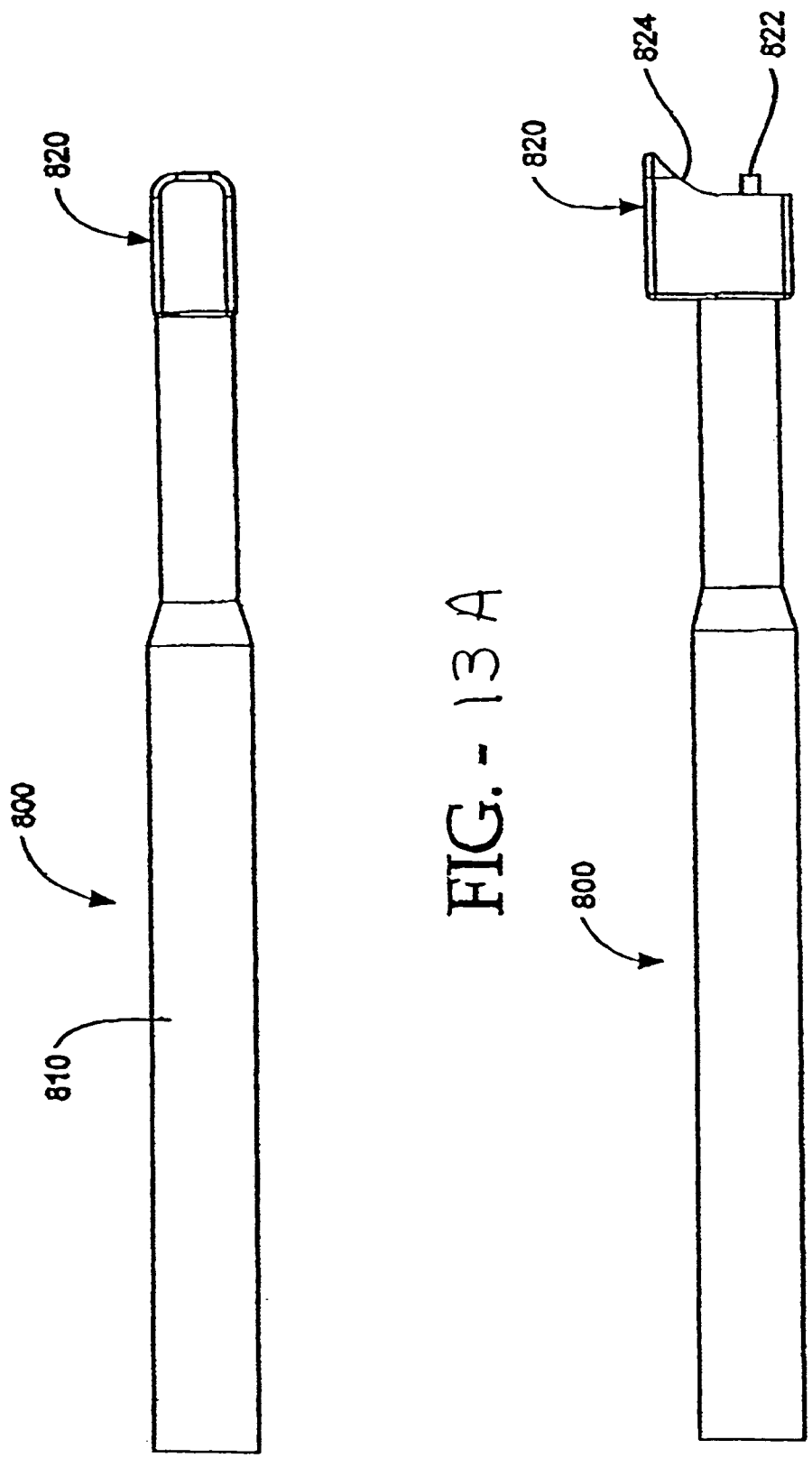
FIG. 13A is a side view of an embodiment of the implant insertion tool of the invention.
FIG. 13B is a top view of the embodiment of the implant insertion tool of the invention.
Figure 13C:
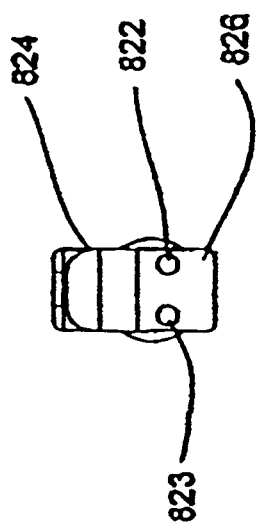
FIG. 13C is a distal end view of the embodiment of the implant insertion tool of the invention.
Figure 13D:
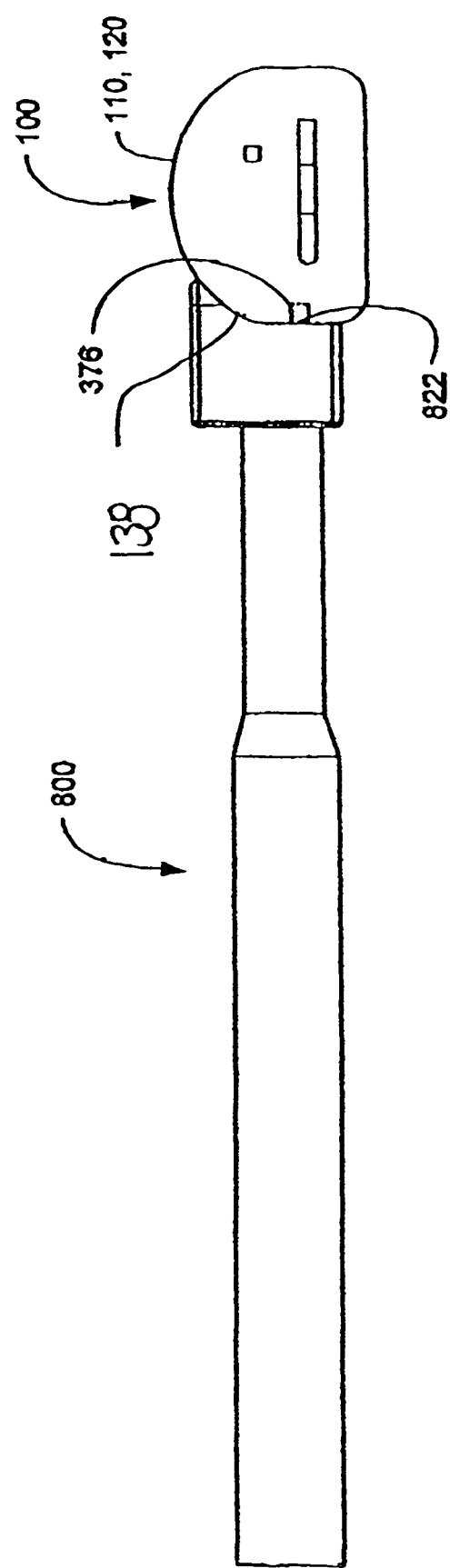
FIG. 13D is a top view of an embodiment of the implant insertion tool holding an embodiment of the implant.

The keel-receiving channels are oriented perpendicular to the sagittal plane of the spine. The implant is then inserted laterally 530 between two vertebrae, with the keels aligned and inserted into the keel-receiving channels. A tool, similar to the one disclosed in application Ser. No. 10/685,134 of James F. Zucherman et al., filed Oct. 14, 2003, and entitled, "Tools for Implanting an Artificial Vertebral Disk and Method," incorporated herein by reference, can be used to position the implant in the intervertebral disk space 535. FIG. 13A depicts the implanting tool used to insert an implant between vertebral bodies. FIG. 13A is a side view of the implantation tool 800 that has a handle 810 and an implant holder 820. The implant holder 820 has an implant conforming surface 824 and two pins 822 for holding a first plate 110 and a second plate 120 of a first half of the implant. The implant nests within a conforming surface 824 and is held by pins 822. FIG. 13C shows the distal view of the end of the tool with two pins 822, 823 for securing the first and second plate of the implant. The tool can be rotated by the user 180° to implant the other half of the implant. A variety of kits can be assembled that include an implant sized for a particular patient. The kit could also include several cutting tools 700 and several implanting tools 800 or a single handle that cooperates with cutting ends 702 and implantation ends 820.

The implant also can be anchored with bone screws if necessary 540. After implantation, the wound is closed 545. This procedure can be followed for either a left lateral approach or right lateral approach.

The disclosed method further can be used for an anterior or posterior approach to insert implant 200 or any implant wherein the keels are oriented substantially parallel to the sagittal plane of the spine. Using an anterior approach, the access step 510 would involve making an incision anteriorly. Keel-receiving channels are cut from an anterior direction to receive first and second keels that are substantially parallel to the sagittal plane of the spine. The implant 200 (or other appropriate implant, as indicated) would be inserted from an anterior approach to align the first and second keels 214, 224 with the keel-receiving channels in the adjacent vertebral bodies. The teeth 215, 225 of the first and second keels 214, 224 would face anteriorly.

Alternatively, using a posterior approach, the access step 510 would involve making an incision posteriorly. The keels 214, 224 would be cut from the posterior of the spine, to create keel-receiving channels that are substantially parallel to the sagittal plane of the vertebrae. The implant 200 would be inserted from a posterior approach to align the keels 214, 224 with the keel-receiving channels in the adjacent vertebral bodies. The teeth 215, 225 of the upper and lower keels 214, 224 would face posteriorly.

What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the embodiments described herein, thereby enabling others skilled in the art to understand the various embodiments and various modifications that are suited to the particular use contemplated. It is intended that the scope of what is disclosed be defined by the following claims and their equivalence.

What is claimed:

1. An intervertebral disk replacement implant, the implant comprising:
    a first endplate including a first exterior surface that abuts a first vertebral body and an opposing first inner surface, the first endplate further including a first anterior side, a first posterior side, a first right lateral side, and a first left lateral side each extending between the first exterior surface and the first opposing inner surface, wherein the first endplate has a first length extending between the first anterior side and the first posterior side and a first width extending between the first right lateral side and the first left lateral side,
    the first exterior surface having at least one first keel extending along a majority of the first width of the first endplate substantially parallel to a first lateral axis extending between the first right and left lateral sides,
    the first opposing inner surface forming a first S-shaped curve in cross section in an anterior-posterior direction defining a first concave portion adjacent the first anterior side and a first convex portion adjacent to the first posterior side, the first concave and convex portions are continuous and smooth with respect to each other to form the first S-shaped curve, and wherein the first inner surface is straight in cross-section in a right-to-left lateral direction from the first right lateral side to the first left lateral side; and
    a second endplate including a second exterior surface that abuts a second vertebral body and an opposing second inner surface, the second endplate further including a second anterior side, a second posterior side, a second right lateral side, and a second left lateral side each extending between the second exterior surface and the opposing second inner surface, wherein the second endplate has a second length extending between the second anterior side and the second posterior side and a second width extending between the second right lateral side and the second left lateral side,
    the second exterior surface having at least one second keel along a majority of the second width of the second endplate substantially parallel to a second lateral axis extending between the second right and left lateral sides,
    the second opposing inner surface forming a second S-shaped curve in cross section in the anterior-posterior direction defining a second concave portion adjacent the second anterior side and a second convex portion adjacent the second posterior side, the second concave and convex portions are continuous and smooth with respect to each other to form the second S-shaped curve, and wherein the second inner surface is straight in cross-section in the right-to-left lateral direction from the second right lateral side to the second left lateral side,
    the second S-shaped curve adapted to mate with the first S-shaped curve formed from the first inner surface, the mating of the first and second S-shaped curves enables the first convex portion to mate with the second concave portion to form a first articulating element, the mating of the first and second S-shaped curves enables the first concave portion to mate with the second convex portion to form a second articulating element, the first and second articulating elements are joined in continuous smooth fashion in the anterior-posterior direction such that when the first and second S-shaped curves are mated the first endplate linearly translates relative to the second endplate in the direction of the first and second lateral axes while allowing the first and second endplates to pivot relative to one another about the first and second articulating elements.

2. The implant in claim 1 wherein the at least one first keel is sized and shaped to anchor the first endplate in the first vertebral body.

3. The implant of claim 2, wherein the at least one first keel extends fully across the first exterior surface.

4. The implant of claim 3, wherein the at least one first keel comprises angled teeth.

5. The implant of claim 1 wherein the at least one second keel is sized and shaped to anchor the second endplate in the second vertebral body.

6. The implant of claim 1 wherein the implant is adapted to be inserted laterally.

7. The implant of claim 1 wherein the implant is adapted to be inserted posteriorly.

8. The implant of claim 1 wherein the implant is adapted to be inserted anteriorly.

9. The implant of claim 1 wherein the first exterior surface has a first lip defining a first bore hole therethrough, the first bore hole is adapted to accept a bone anchor to secure the first endplate to the first vertebral body; and the second exterior surface has a second lip defining a second bore hole therethrough, the second bore hole adapted to secure the second endplate to the second vertebral body.

10. The implant of claim 1, wherein the first keel extends across the first exterior surface in the right-to-left lateral direction.

11. An intervertebral disk replacement implant adapted to be inserted between adjacent vertebrae, the implant comprising:
    a first endplate including a first exterior surface and first inner surface, wherein the first inner surface includes a first projection and a first depression together forming an S-shape in cross section in an anterior-posterior direction, and wherein the first inner surface is straight in cross section in a right-to-left lateral direction;
    the first endplate having an overall length extending in the anterior-posterior direction and an overall width extending in the right-to-left lateral direction;
    the first exterior surface having at least one first keel extending along a majority of the overall width of the first endplate substantially parallel to a lateral axis extending across the overall length of the first endplate;
    a second endplate including a second exterior surface and a second inner surface, wherein the second inner surface includes a second projection and a second depression together forming an S-shape in cross section in the anterior-posterior direction, and wherein the second inner surface is straight in cross section in the right-to-left lateral direction, the second inner surface mating with the first inner surface to form a first articulating element and a second articulating element that is inverted with respect to the first articulating element, the two articulating elements being in an anterior-posterior orientation and allowing spinal motion in a plurality of directions such that when the first and second articulating elements are formed the first endplate linearly translates relative to the second endplate in the lateral direction;

the first articulating element is comprised of the first projection mated with the second depression; and the second articulating element comprises the first depression mated with the second projection.

12. The implant of claim 11 wherein the first articulating element and the second articulating element allow bending from flexion and extension of the spine.

13. The implant of claim 11 wherein the first articulating element and the second articulating element allow rotational and lateral motion of the spine.

14. The implant of claim 11, wherein the first projection and the first depression are formed of cylindrical surfaces and the second projection and second depression are formed of cylindrical surfaces.

15. An intervertebral disk replacement implant adapted to be inserted laterally between adjacent vertebrae, the implant comprising:
  a first endplate having:
    a first exterior surface adapted to mate with a first vertebral body;
    a first inner surface having a first projection and a first depression together forming an S-shape in cross section in an anterior-posterior direction, and wherein the first inner surface is straight in cross section in a right-to-left lateral direction;
    at least one first keel adapted to anchor the first endplate in the first vertebral body;
    wherein the first endplate has an overall length extending in the anterior-posterior direction and an overall width extending in the right-to-left lateral direction, the at least one first keel extending along a majority of the overall width of the first endplate substantially parallel to a lateral axis extending across the overall length of the first endplate;
  a second endplate having:
    a second exterior surface adapted to mate with a second vertebral body;
    a second inner surface opposing and mating with the first inner surface,
    wherein the second inner surface has a second projection and a second depression together forming an S-shape in cross section in the anterior-posterior direction, and wherein the second inner surface is straight in cross section in the right-to-left lateral direction;
    at least one second keel adapted to anchor the second endplate to the second vertebral body;
  a first articulating element comprising the first projection and the second depression; and
  a second articulating element comprising the first depression and the second projection and oriented in an anterior-posterior direction with the first articulating element,
  wherein the first and second articulating elements are adapted to permit pivoting about a pivot point to facilitate movement of the spine in a plurality of directions, and wherein when the first and second inner surfaces are mated the first endplate linearly translates in the lateral direction relative to the second endplate.

16. The implant of claim 15 wherein the first projection and the first depression are cylindrical and the second projection and second depression are cylindrical.

17. An intervertebral disk replacement implant including a first endplate having a first inner surface, and a second endplate having a second inner surface that opposes the first inner surface, the improvement comprising:
  the first inner surface is S-shaped in cross-section in an anterior-posterior direction, and wherein the first inner surface is straight in cross-section in a right-to-left lateral direction;
  the second endplate is inversely S-shaped in cross-section in the anterior-posterior direction, wherein the second inner surface is straight in cross-section in the right-to-left lateral direction, and wherein the second inner surface is adapted to mate with the first inner surface,
  the first endplate having an overall length extending in the anterior-posterior direction and an overall width extending in the right-to-left lateral direction;
  the first exterior surface having at least one first keel extending along a majority of the overall width of the first endplate substantially parallel to a lateral axis extending across the overall length of the first endplate;
  wherein when the first and second S-shaped curves are mated the first endplate linearly translates relative to the second endplate in the direction of the lateral axis while allowing the first and second endplates to pivot relative to one another in the anterior-posterior direction.

* * * * *

UNITED STATES PATENT AND TRADEMARK OFFICE
CERTIFICATE OF CORRECTION

PATENT NO. : 7,575,600 B2  Page 1 of 1
APPLICATION NO. : 11/003624
DATED : August 18, 2009
INVENTOR(S) : Zucherman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1158 days.

Signed and Sealed this

Seventh Day of September, 2010

David J. Kappos
*Director of the United States Patent and Trademark Office*